US012661416B2

(12) United States Patent
Frangioni et al.

(10) Patent No.: US 12,661,416 B2
(45) Date of Patent: Jun. 23, 2026

(54) COMBINATIONS OF IMAGING AGENT CONJUGATES AND APPLICATION THEREOF

(71) Applicant: Curadel Surgical Innovations, Inc., Natick, MA (US)

(72) Inventors: John V. Frangioni, Weston, MA (US); Wolfgang Maison, Winsen (DE)

(73) Assignee: Curadel Surgical Innovations, Inc., Bonita Springs, FL (US)

( * ) Notice: Subject to any disclaimer, the term of this patent is extended or adjusted under 35 U.S.C. 154(b) by 0 days.

(21) Appl. No.: 18/640,620

(22) Filed: Apr. 19, 2024

(65) Prior Publication Data

US 2025/0082795 A1 Mar. 13, 2025

Related U.S. Application Data

(60) Provisional application No. 63/538,038, filed on Sep. 12, 2023.

(51) Int. Cl.

*A61K 51/04* (2006.01)
*A61B 6/03* (2006.01)
*A61K 49/00* (2006.01)
*A61K 51/08* (2006.01)

(52) U.S. Cl.

CPC .......... *A61K 51/0482* (2013.01); *A61B 6/037* (2013.01); *A61K 49/0032* (2013.01); *A61K 51/0478* (2013.01); *A61K 51/082* (2013.01); *A61K 2121/00* (2013.01); *A61K 2123/00* (2013.01)

(58) Field of Classification Search

CPC ............ A61K 51/0482; A61K 49/0032; A61K 51/0478; A61K 51/082; A61B 6/037
USPC ........................................................ 424/1.69
See application file for complete search history.

(56) References Cited

U.S. PATENT DOCUMENTS

| | | | |
|---|---|---|---|
| 6,083,485 | A | 7/2000 | Licha et al. |
| 6,258,340 | B1 | 7/2001 | Licha et al. |
| 6,440,389 | B1 | 8/2002 | Rabito |
| 6,913,743 | B2 | 7/2005 | Licha et al. |
| 6,926,885 | B2 | 8/2005 | Licha et al. |
| 7,025,949 | B2 | 4/2006 | Licha et al. |
| 7,445,767 | B2 | 11/2008 | Licha et al. |
| 7,582,483 | B2 | 9/2009 | Mizutani et al. |
| 7,655,217 | B2 | 2/2010 | Licha et al. |
| 7,682,603 | B2 | 3/2010 | Hammer et al. |
| 8,173,819 | B2 | 5/2012 | Rajopadhye et al. |
| 8,268,014 | B2 | 9/2012 | Frohling |
| 8,460,639 | B2 | 6/2013 | Nomoto et al. |
| 10,201,621 | B2 | 2/2019 | Frangioni et al. |
| 11,279,698 | B2 | 3/2022 | Babich et al. |
| 2001/0055567 | A1 | 12/2001 | Licha et al. |
| 2003/0026762 | A1 | 2/2003 | Malmros et al. |
| 2003/0026763 | A1 | 2/2003 | Licha et al. |
| 2003/0170179 | A1 | 9/2003 | Licha et al. |
| 2004/0028611 | A1 | 2/2004 | Frangioni |
| 2004/0029837 | A1 | 2/2004 | Fries et al. |
| 2004/0062713 | A1 | 4/2004 | Matsuo et al. |
| 2005/0106106 | A1 | 5/2005 | Licha et al. |
| 2005/0169844 | A1 | 8/2005 | Licha et al. |
| 2006/0040400 | A1 | 2/2006 | Mizutani et al. |
| 2006/0165598 | A1 | 7/2006 | Licha et al. |
| 2006/0165599 | A1 | 7/2006 | Licha et al. |
| 2006/0275209 | A1 | 12/2006 | Schweiger et al. |
| 2007/0292883 | A1 | 12/2007 | Ossovskaya et al. |
| 2008/0308744 | A1 | 12/2008 | Frangioni et al. |
| 2008/0318336 | A1 | 12/2008 | Scherninski et al. |
| 2009/0269277 | A1 | 10/2009 | Chang et al. |
| 2010/0035871 | A1 | 2/2010 | Stack et al. |
| 2010/0129293 | A1 | 5/2010 | Licha et al. |
| 2010/0323389 | A1 | 12/2010 | Xu et al. |
| 2012/0017931 | A1 | 1/2012 | Frohling |
| 2012/0045851 | A1 | 2/2012 | Scherninski et al. |
| 2013/0030282 | A1 | 1/2013 | Margel et al. |
| 2014/0063097 | A1 | 3/2014 | Liu et al. |
| 2015/0209451 | A1 | 7/2015 | Frangioni et al. |
| 2017/0290927 | A1 | 10/2017 | Frangioni et al. |

(Continued)

FOREIGN PATENT DOCUMENTS

| | | | |
|---|---|---|---|
| JP | H5-150395 | A | 6/1993 |
| JP | 2000-95758 | A | 4/2000 |
| JP | 2005-524072 | A | 8/2005 |

(Continued)

OTHER PUBLICATIONS

Vahrmeijer et al. Nat. Rev. Clin. Oncol. 10, 507-518 (Year: 2013).*
Scheltinga et al. J. Nucl. Med. 2011, 52, 1778-1785. (Year: 2011).*
Fan et al. Nat. Nanotech. 2018, 13, 941-946. (Year: 2018).*
Ciba-Geigy AG, "Use of dyes for shading during optical brightening of polyester and polyacrylonitrile substrates", Research Disclosure, 1982, vol. 216, Article No. 21611, pp. 107-109.
Yuan, L. et al. "A unique class of near-infrared functional fluorescent dyes with carboxylic-acid-modulated fluorescence ON/OFF switching rational design, synthesis, optical properties, theoretical calculations, and applications for fluorescence imaging in living animals", Journal of the American Chamical Society, 2012, vol. 134, No. 2, pp. 1200-1211.
James, N.S. et al., "Evaluation of polymethine dyes as potential probes for near infrared fluorescence imaging of tumors: Part 1", Theranostics, Aug. 2013, vol. 3, No. 9, pp. 692-702.

(Continued)

*Primary Examiner* — Michael G. Hartley
*Assistant Examiner* — Sean R Donohue
(74) *Attorney, Agent, or Firm* — Troutman Pepper Locke LLP; Gabrielle L. Gelozin

(57) ABSTRACT

The present invention provides a combination of two or more imaging agent conjugates comprising an imaging agent conjugated to a targeting ligand, wherein the imaging agent comprises one or more of ZW800-1, ZW830-1, ZW700-1-Forte, ZW-DOTA, ZW-PyC3A, ZW-Macropa, ZW-porphyrin, ZW-NOTA, and ZW-Deferoxamine; and the targeting ligand comprises one or more of a cRGD, a dPSMA-617 or a KUE, a FAP, a bombesin receptor binding vector, or a octreotide binding vector, or one or more of peptides selected from SEQ ID No: 1-4.

6 Claims, 5 Drawing Sheets

Specification includes a Sequence Listing.

(56) References Cited

U.S. PATENT DOCUMENTS

| | | | | |
|---|---|---|---|---|
| 2017/0290928 | A1 * | 10/2017 | Frangioni | A61K 49/0032 |
| 2022/0387631 | A1 | 12/2022 | Frangioni et al. | |

FOREIGN PATENT DOCUMENTS

| | | | | |
|---|---|---|---|---|
| JP | 2007-508282 A | 4/2007 | | |
| JP | 2009-507035 A | 2/2009 | | |
| JP | 2010-169677 A | 8/2010 | | |
| JP | 2011-503067 A | 1/2011 | | |
| JP | 2012-524153 A | 10/2012 | | |
| JP | 2013-523725 A | 6/2013 | | |
| JP | 2013-199477 A | 10/2013 | | |
| WO | 2005/082423 A2 | 9/2005 | | |
| WO | 2007/017602 A2 | 2/2007 | | |
| WO | 2009/061473 A2 | 5/2009 | | |
| WO | 2010/091243 A1 | 8/2010 | | |
| WO | WO-2010108125 A2 | * | 9/2010 | A61K 49/0032 |
| WO | 2010/121163 A2 | 10/2010 | | |
| WO | 2012/063028 A1 | 5/2012 | | |
| WO | 2015066290 A1 | 5/2015 | | |
| WO | WO-2022212958 A1 | * | 10/2022 | A61K 49/0032 |

OTHER PUBLICATIONS

Quek, C.-H. et al. "Near-infrared fluorescent nanoprobes for in vivo optical imaging", Nanomaterials, 2012, vol. 2, No. 2, pp. 92-112.
Ashitate, Y., et al. "Simultaneous mapping of pan and sentinel lymph nodes for real-time image guided surgery", Teranostics, Apr. 2014, vol. 4, No. 7, pp. 693-700.
Amiot, C. L. et al., "Near-infrared fluorescent materials for sensing of biological targets", Sensors, 2008, vol. 8, No. 5, pp. 3082-3105.
Tibre, A. G. J. et al., "Imaging technique implemented in CellTracks system," Cytometry, 2002, vol. 47, No. 4, pp. 248-255.
Chemical Physics Letters, Mar. 1996, vol. 250 pp. 261-265.
Gibbs "Near infrared fluorescence for image-guided surgery" Quant Imaging Med Surg, Jan. 1, 2012, pp. 177-187.
Journal of Photopolymer Science and Technology, 2000, vol. 13, No. 2, pp. 183-186.
Proceedings of SPIE, 2011, vol. 8114, pp. 81140 T-1 to 81140 T-9.
Sano, K. "Short PEG-linkers improve the performance of targeted, activable monoclonal antibody-indocyanine green optical imaging probes" Bioconjugate Chemistry, 2013 24(5), pp. 811-816.
European Journal of Medicinal Chemistry, 2012, vol. 54, pp. 647-659.
Office Action issued in Japanese Patent Application No. JP 2016-552234, dated Oct. 21, 2020.
Stoermer U et al., "Kann der metachromatische Index eine Hilfe bei der Krebsdiagnose sein?// The metachromatic index—an aid in cancer diagnosis?", Acta Histochemica, vol. 84, No. 1, Jan. 1, 1988, pp. 31-39.
Zimmermann U et al., "[Staining behavior and applicability of spectrally pure Capriblue GN, Stella Blue, Oxonin and Punky Blue]", Acta Histochemica, 1983, vol. 72, No. 1, pp. 55-69.
Winer, J. H., et al., "Intraoperative Localization of Insulinoma and Normal Pancreas Using Invisible Near-Infrared Fluorescent Light", Annals of Surgical Oncology, vol. 17, No. 4, Dec. 22, 2009, pp. 1094-1100.
Kate, P. G., et al., "Rapid and Selective Targeting of Heterogeneous Pancreatic Neuroendocrine Tumors", iScience, Apr. 24, 2020, pp. 101006-101006.
Extended European Search Report dated Feb. 13, 2023, issued during the prosecution of European Patent Application No. EP 22188587.4.
Ghanadzadeh et al. (Spectrochimica Acta Part A 2009, 73, 324-329).
Dao et al. (Australas. Phys. Eng. Sci. Med. 2004, 27, 224-229).
Sloviter (Cancer Res. 1949, 9, 677-680).
International Search Report issued in PCT/US2014/063104, dated Feb. 26, 2015.
International Search Report issued in PCT/US2014/063097, dated Apr. 10, 2015.
A. Swierzewski et. al., DOTA-and DFO-Based Zwitterionic Chelators for 89ZR-PET), Universitat Hamburg, Fachbereich Chemie, Institute fur Pharmazie.
T. Lindner, et al., Radioligands Targeting Fibroblast Activation Protein (FAP)), Cancer 2021, 13, 5744.
Valk et al. (Clin. Cancer Res. 2020, 26, 3990-3998 and supplemental data).
Bao et al., (Chem. Commun. 2017, 53, 1611-1614.
Mulder et al. (Am Jnl. Nucl. Med. Mol. Imaging 2018, 8, 282-291).
De Jalon et al. (Mol. Imaging and Biol. 2023, 25, 144-155.
Hyun et al. (Mol. Imaging Biol. 2016, 18, 52-61).
Hensbergen et al. (Bioconj. Chem. 2020, 31, 375-395).
Njiojob et al. (J. Med. Chem. 2015, 58, 2845-2854).
Van Rymenant et al. (Frontier Chem. 2021, Article 640566, p. 1-12.
Slania et al. (J. Med. Chem 2021, 64, 4059-4070.
Park et al., Rapid & Selective Targeting of Heterogenous Pancreatic Neuroendocrine Tumors, IScience, 23, 101006, Apr. 24, 2020.

* cited by examiner $(ZWI)_4$-DOTA $(ZWI)_2$-macropa $(ZWI)_4$-porphyrin $(ZWI)_3$-NOTA $(ZWI)_3$-PyC3A

ZWI = or $(ZWI)_4$-DFO*

(ZWI)$_3$-DOTA-tv (ZWI)$_2$-macropa-tv (ZWI)$_3$-porphyrin-tv (ZWI)$_2$-NOTA-tv (ZWI)$_3$-PYC$_3$A-tv

ZWI = or (ZWI)$_4$-DFO-tv

KUE dPSMA-617 cRGD

Scheme 2

(ZWI)$_3$-DOTA-AHX-KUE

Scheme 7

```
                         SEQUENCE LISTING


Sequence total quantity: 6
SEQ ID NO: 1            moltype = AA  length = 9
FEATURE                 Location/Qualifiers
source                  1..9
                        mol_type = protein
                        organism = Homo sapiens
SEQUENCE: 1
CGQKRTRGC                                                         9

SEQ ID NO: 2            moltype = AA  length = 12
FEATURE                 Location/Qualifiers
source                  1..12
                        mol_type = protein
                        organism = Homo sapiens
SEQUENCE: 2
HTMYYHHYQH HL                                                     12

SEQ ID NO: 3            moltype = AA  length = 9
FEATURE                 Location/Qualifiers
source                  1..9
                        mol_type = protein
                        organism = Homo sapiens
SEQUENCE: 3
CRKRLDRNC                                                         9

SEQ ID NO: 4            moltype = AA  length = 6
FEATURE                 Location/Qualifiers
source                  1..6
                        mol_type = protein
                        organism = Homo sapiens
SEQUENCE: 4
CSPGAK                                                            6

SEQ ID NO: 5            moltype = AA  length = 8
FEATURE                 Location/Qualifiers
source                  1..8
                        mol_type = protein
                        organism = Homo sapiens
SEQUENCE: 5
FCFWKTCT                                                          8

SEQ ID NO: 6            moltype = AA  length = 14
FEATURE                 Location/Qualifiers
source                  1..14
                        mol_type = protein
                        organism = Homo sapiens
SEQUENCE: 6
XQRLGNQWAV GHLM                                                   14
```

COMBINATIONS OF IMAGING AGENT CONJUGATES AND APPLICATION THEREOF

CROSS-REFERENCE TO RELATED APPLICATIONS

This application claims priority to U.S. Provisional Patent Application Ser. No. 63/538,038 filed Sep. 12, 2023, the disclosure of which is incorporated herein by reference.

SEQUENCE LISTING

A Sequence Listing conforming to the rules of WIPO Standard ST.26 is hereby incorporated by reference. Said Sequence Listing has been filed as an electronic document via PatentCenter encoded as XML in UTF-8 text. The electronic document, created on Apr. 17, 2024, is entitled "1515138109US0_SL.xml", and is 6,026 bytes in size.—

FIELD OF THE INVENTION

The present invention relates to combinations of imaging agent conjugates and their use as imaging, diagnostic, chemical processing, and treatment agents. These combinations of imaging agent conjugates enable a simultaneous detection of multiple targets in a biological subject, and/or provide improved detection of cells that might be lacking one or more targets.

BACKGROUND OF THE INVENTION

Current imaging techniques, like magnetic resonance imaging (MRI), single-photon emission computed tomography (SPECT), or positron emission tomography (PET), permit the detection of diseases at the cellular level. Imaging agents have been designed to assist these imaging techniques. These imaging agents typically have a targeting ligand which specifically recognizes a particular target, and an imaging dye which provides a uniformed light signal having a particular emission wavelength upon recognizing the particular target.

However, in clinical practice, it is often necessary that more than one target in a biological subject to be simultaneously detected. Cancer cells, for example, are often heterogeneous in target expression so using only a single targeted contrast agent may not label some tumors even in the same subject. Moreover, a single emission wavelength may not be enough to provide a sufficient light signal when used for optical surgical navigation.

As such, there remains a need for new and improved imaging agents which enables a simultaneous detection of multiple targets in a biological subject, and/or provide improved detection of cells that might be lacking one or more targets. The combinations of the imaging agent conjugates of the invention are directed toward these and other needs.

SUMMARY OF THE INVENTION

This invention provides for a combination of imaging agent conjugates which are useful for biological imaging and medical treatment. These combinations of imaging agent conjugates enable simultaneous detection of multiple targets in a biological subject, improved detection of cells that might be lacking one or more targets, and provide improved in vivo properties which help improve the signal-to-background ratio of imaged tissues and the therapeutic window of treated tissue, while allowing for easier and more efficient clearance by the subject.

In one aspect, the invention provides a composition comprising a combination of two or more imaging agents, zwitterionic metal chelator complexes, or combinations thereof.

In one embodiment, the composition comprises a combination of two or more selected from the group consisting of cRGD-ZW800-1, KUE-ZW800-1, FAP-ZW800-1, bombesin-ZW800-1, octreotide-ZW800-1; cRGD-ZW700-1 Forte, KUE-ZW700-1 Forte, FAP-ZW700-1 Forte, bombesin-ZW700-1 Forte, octreotide-ZW700-1 Forte; cRGD-ZW830-1, KUE-ZW830-01, FAP-ZW830-1, bombesin-ZW830-1, octreotide-ZW830-1; cRGD-ZW-DOTA, KUE-ZW-DOTA, FAP-ZW-DOTA, bombesin-ZW-DOTA, octreotide-ZW-DOTA; cRGD-ZW-PyC3A, KUE-ZW-PyC3A, FAP-ZW-PyC3A, bombesin-ZW-PyC3A, octreotide-ZW-PyC3A; cRGD-ZW-Macropa, KUE-ZW-Macropa, FAP-ZW-Macropa, bombesin-ZW-Macropa, octreotide-ZW-Macropa; cRGD-ZW-porphyrin, KUE-ZW-porphyrin, and, FAP-ZW-porphyrin, bombesin-ZW-porphyrin, octreotide-ZW-porphyrin; cRGD-ZW-NOTA, KUE-ZW-NOTA, FAP-ZW-NOTA, bombesin-ZW-NOTA, octreotide-ZW-NOTA; cRGD-ZW-Deferoxamine, KUE-ZW-Deferoxamine, FAP-ZW-Deferoxamine, bombesin-ZW-Deferoxamine, and octreotide-ZW-Deferoxamine.

In one embodiment, the composition comprises a combination of three or more selected from the group consisting of cRGD-ZW800-1, KUE-ZW800-1, FAP-ZW800-1, bombesin-ZW800-1, octreotide-ZW800-1; cRGD-ZW700-1 Forte, KUE-ZW700-01 Forte, FAP-ZW700-1 Forte, bombesin-ZW700-1 Forte, octreotide-ZW700-1 Forte; cRGD-ZW830-1, KUE-ZW830-01, FAP-ZW830-1, bombesin-ZW830-1, octreotide-ZW830-1; cRGD-ZW-DOTA, KUE-ZW-DOTA, FAP-ZW-DOTA, bombesin-ZW-DOTA, octreotide-ZW-DOTA; cRGD-ZW-PyC3A, KUE-ZW-PyC3A, FAP-ZW-PyC3A, bombesin-ZW-PyC3A, octreotide-ZW-PyC3A; cRGD-ZW-Macropa, KUE-ZW-Macropa, FAP-ZW-Macropa, bombesin-ZW-Macropa, octreotide-ZW-Macropa; cRGD-ZW-porphyrin, KUE-ZW-porphyrin, FAP-ZW-porphyrin, bombesin-ZW-porphyrin, octreotide-ZW-porphyrin; cRGD-ZW-NOTA, KUE-ZW-NOTA, FAP-ZW-NOTA, bombesin-ZW-NOTA, octreotide-ZW-NOTA; cRGD-ZW-Deferoxamine, KUE-ZW-Deferoxamine, FAP-ZW-Deferoxamine, bombesin-ZW-Deferoxamine, and octreotide-ZW-Deferoxamine.

In one embodiment, the composition comprises a combination of:

a. cRGD-ZW800-1, KUE-ZW800-1, and FAP-ZW800-1;
b. cRGD-ZW700-1 Forte, KUE-ZW700-1 Forte, and FAP-ZW700-1 Forte;
c. cRGD-ZW830-1, KUE-ZW830-1, and FAP-ZW830-1;
d. cRGD-ZW800-1, and KUE-ZW700-1 Forte;
e. KUE-ZW800-1, and cRGD-ZW700-1 Forte;
f. KUE-ZW800-1, and FAP-ZW700-1 Forte;
g. FAP-ZW800-1, and KUE-ZW700-1 Forte;
h. FAP-ZW800-1, and cRGD-ZW700-1 Forte;
i. cRGD-ZW800-1, and FAP-ZW700-1 Forte;
j. cRGD-ZW-DOTA-Cu-64, KUE-ZW-DOTA-Cu-64, and FAP-ZW-DOTA-Cu-64; or
h. cRGD-ZW-DOTA-Lu-177, KUE-ZW-DOTA-Lu-177, and FAP-ZW-DOTA-Lu-177.

In one aspect, the invention provides a method of imaging cells. The method comprises (a) contacting cells with a composition aforementioned, (b) irradiating the cells at a wavelength absorbed by the imaging agent; and (c) and detecting a signal from the imaging agent, thereby imaging the cells.

In one embodiment, the composition for imaging cells comprises a combination of:

a. cRGD-ZW800-1, KUE-ZW800-1, and FAP-ZW800-1;
b. cRGD-ZW700-1 Forte, KUE-ZW700-1 Forte, and FAP-ZW700-1 Forte;
c. cRGD-ZW830-1, KUE-ZW830-1, and FAP-ZW830-1;
d. cRGD-ZW800-1, and KUE-ZW700-1 Forte;
e. KUE-ZW800-1, and cRGD-ZW700-1 Forte;
f. KUE-ZW800-1, and FAP-ZW700-1 Forte;
g. FAP-ZW800-1, and KUE-ZW700-1 Forte;
h. FAP-ZW800-1, and cRGD-ZW700-1 Forte; or
i. cRGD-ZW800-1, and FAP-ZW700-1 Forte.

In one embodiment, the cells are tumor cells, inflammatory cells, or cells undergoing angiogenesis.

In one embodiment, the imaging agent is administered to an organism comprising or suspected of comprising the cells.

In one embodiment, the organism is human.

In one embodiment, the imaging agent has peak absorbance at about 600 nm to 850 nm.

In one embodiment, the tissue or cells is imaged in vivo.

In yet another aspect of the invention, a method of producing an image of a target object comprises (a) contacting the target object with a composition agent according to Claim 1, (b) measuring the signal from the target object after contact with the composition using positron emission tomography (PET), single-photon emission computerized tomography (SPECT), or magnetic resonance imaging (MRI); and (c) and generating an image of the target object based on the signal measured.

In one embodiment, the composition for producing an image of a target object comprises a combination of cRGD-ZW-DOTA-Cu-64, KUE-ZW-DOTA-Cu-64, and FAP-ZW-DOTA-Cu-64.

In yet another aspect of the invention, a method of treating a subject with radiotherapy comprises administering a therapeutically effective amount of a composition agent to a patient in need of such treatment.

In one embodiment, the composition for treating a subject with radiotherapy comprises a combination of cRGD-ZW-DOTA-Lu-177, KUE-ZW-DOTA-Lu-177, and FAP-ZW-DOTA-Lu-177.

In yet another aspect of the invention, a radiosurgical method for treating a patient body comprises receiving a desired lesion pattern and planned radiation distribution; administering an effective amount of a composition according to Claim 1 to the subject to effectively image the desired lesion pattern; performing surgery on the desired lesion pattern to treat the patient body.

In one embodiment, the zwitterionic metal chelator of the diagnostic agent further comprises one or more targeting vectors wherein the one or more targeting vectors are cRGD, dPSMA-617, KUE, FAP, octreotide, bombesin, or a homo- or hetero-dimer formed from their combination.

In one embodiment, the desired lesion pattern is received from a user interface of a treatment planning module.

In one embodiment, the treatment planning module is pre-programmed with specifications for various disease states and cancerous conditions.

In one embodiment, the treatment planning module identifies lesion patterns for various disease states and cancerous conditions using artificial intelligence data.

In one embodiment, the surgery is performed using a stereotactic radiosurgical system.

In yet another aspect of the invention, a method of treating a cancer by administering an effective amount of aforementioned composition, wherein the method comprises a step to diagnose the cancer and a step of administering the therapeutic agent to a subject determined to be in need thereof. The step to diagnose the cancer comprises contacting cells, tissues or organs of a subject with an imaging agent, imaging the cells, tissues, or organs of the subject using positron emission tomography (PET), single-photon emission computerized tomography (SPECT), or magnetic resonance imaging (MRI), and diagnosing the cancer in the cells tissues, or organs of the subject based on imaging data collected; and wherein the therapeutic agent aforementioned comprises at least one zwitterionic metal chelator wherein the metal atom complexed to the zwitterionic metal chelator is a radioactive metal isotope known to emit ionizing radiation that results in the death of cells that take up the analogs; or a non-radioactive metal that is capable of releasing cytotoxic radiation upon irradiation with alpha emission, beta emission, neutron capture, or a combination thereof.

DETAILED DESCRIPTION

Figure 1:
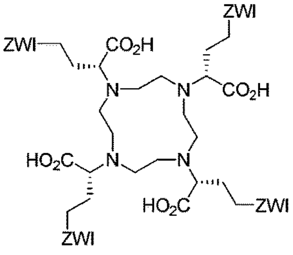
FIG. 1 is a representation of seven imaging agents comprising non-targeted zwitterionic metal chelators according to the invention.
Figure 1:
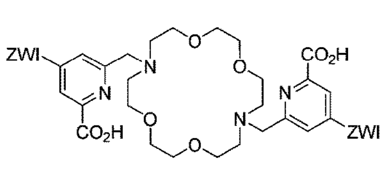
Figure 1:
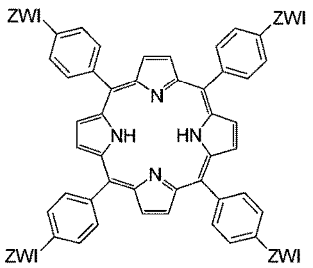
Figure 1:
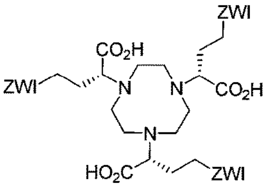
Figure 1:
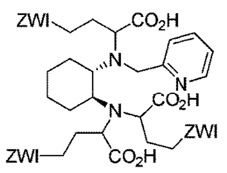
Figure 1:
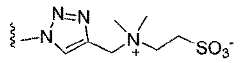
Figure 1:
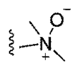
Figure 1:
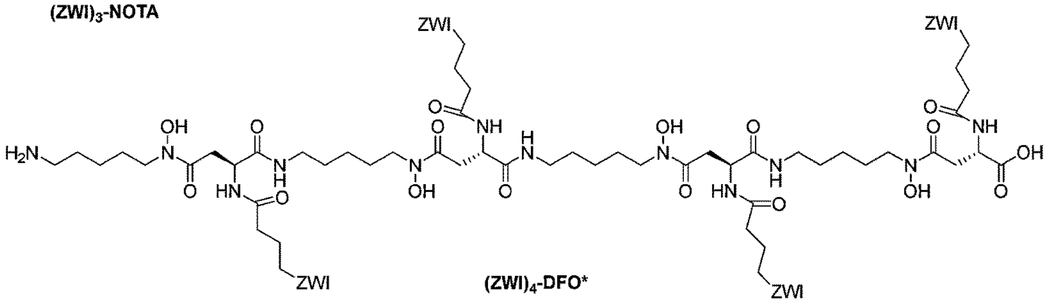

The present disclosure relates, inter alia, to combinations of imaging agent conjugates and/or therapeutic agent conjugates which have an imaging agent dye having metal chelators conjugates to a target ligand. One or more of the imaging agent conjugates of a combination of the disclosure includes an imaging agent dye and/or a target ligand different from the other imaging agent conjugates of the combination. Therefore, combinations are capable for simultaneous detection of more than one target, improved detection of cells that might be lacking one or more targets, and/or providing improved light signal for a particular target. The agents described herein are useful in, for example, the detection of abnormal or diseased biological tissues and cells.

Definitions and Additional Embodiments

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish, parasites, microbes, and the like.

As used herein, the term "administration" or "administering" of the subject compound refers to providing a combination composition of the invention and/or prodrugs thereof to a subject in need of diagnosis or treatment.

As used herein, the term "targeting vector" or "targeting ligand" refers to a moiety which is bound to or coordinated to the imaging agents or zwitterionic metal chelators of the combination compositions of the invention to provide enhanced binding to particular cell types or an increased concentration in the presence of particular cell types. In certain embodiments, the targeting vector can be bound to the imaging agents or zwitterionic metal chelators of the combination compositions in addition to the zwitterionic groups thereon. In still other embodiments, the targeting vector can be bound to the zwitterionic metal chelator in place of one or more zwitterionic groups provided that the zwitterionic metal chelator retains at least one zwitterionic group.

As used herein, the term "therapeutic window" or "therapeutic index" refers to the relationship between the therapeutic and toxic dose of a given drug and is calculated using the $ED_{50}$ and $TD_{50}$ (Therapeutic Index=$TD_{50}/ED_{50}$). In certain embodiments of the invention, the zwitterionic metal chelators of the invention have a higher therapeutic index relative to other metal chelators. In certain other embodiments, the therapeutic window refers to a certainty safety factor (CSF) which is defined herein as the ratio of [$TD_1/ED_{99}$]. A CSF>1 indicates that the dose effective in 99% of the population is less than the dose that would be toxic in 1% of the population. In certain embodiments of the invention, the combination compositions of the invention have a higher CSF relative individual active agents.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "combination" refers to a mixture of more than one type of compounds.

As used herein, the term "contacting" refers to the bringing together of substances in physical contact such that the substances can interact with each other. For example, when an agent is "contacted" with tissue or cells, the tissue or cells can interact with the agent, for example, allowing the possibility of binding interactions between the agent and molecular components of the tissue or cells. "Contacting" is meant to include the administration of a substance such as an agent of the invention to an organism. Administration can be, for example, oral or parenteral.

As used herein, the term "ionic group" refers to a moiety comprising one or more charged substituents. The "charged substituent" is a functional group that is generally anionic or cationic when in substantially neutral aqueous conditions (e.g. a pH of about 6.5 to 8.0 or about physiological pH (7.4)). As recited above, examples of charged anionic substituents include anions of inorganic and organic acids such as sulfonate ($—SO_3^{1-}$), oxide, sulfinate, carboxylate, phosphinate, phosphonate, phosphate, and esters (such as alkyl esters) thereof. In some embodiments, the charged substituent is sulfonate or oxide. Examples of charged cationic substituents include quaternary ammonium ions ($—NR_3^+$) and phosphonium ions ($—PR_3^+$), where R is independently selected from $C_{1-6}$ linear alkyl, $C_{4-6}$ branched alkyl, $C_{3-6}$ cycloalkyl, aryl, heteroaryl and arylalkyl or heteroarylalkyl. Other charged cationic substituents include protonated primary, secondary, and tertiary amines, and as well as guanidinium or amidinium or pyridinium or other protonated, alkylated or oxygenated nitrogen heterocycles. In some embodiments, the charged substituent is $—N(CH_3)_3^+$.

As used herein, the phrase "non-ionic oligomeric or polymeric solubilizing groups" refers to soluble polymers such as, for example, polyethylene glycol, polypropylene glycol, polyethylene oxide and propylene oxide copolymer, a carbohydrate, a dextran, polyacrylamide, a peptide and the like. The solubilizing group can be attached by any desired mode. The point of attachment can be, e.g., a carbon-carbon bond, a carbon-oxygen bond, or a nitrogen-carbon bond. The attachment group can be, e.g., an ester group, a carbonate group, an urea group, an alcohol group, an ether group, a sulfide group, an amino group, an alkylene group, an alkyne group, an azide group, a tetrazine, an amide group, a carbonyl group, or a phosphate group.

Some examples of solubilizing groups include polyethylene glycols, such as $—(CH_2CH_2O)_a—H$, $—OC(═O)O(CH_2CH_2O)_aH$, $—OC(═O)O(CH_2CH_2O)_aCH_3$, $—O(CH_2CH_2O)_aCH_3$, and $—S(CH_2CH_2O)_2CH_3$, "a" being an integer between about 2 and about 25O. In some embodiments, "a" is 4 to 12 or 5 to 10. In further embodiments, "a" is 6, 7, or 8. Other examples of solubilizing groups include dextrans such as —OC(═O)O(dextran).

The solubilizing moiety can have an absolute molecular weight of from about 500 amu to about 100,000 amu, e.g., from about 1,000 amu to about 50,000 amu or from about 1,500 to about 25,000 amu.

Further examples of solubilizing groups include: $—(CH_2)_c—(OCH_2CH_2)_d—OR^a$, wherein "c" is 0 to 6, "d"

is 1 to 200, and $R^a$ is H or $C_{1-6}$ alkyl. In some embodiments, "c" is 1 to 4, "d" is 1 to 10, and $R^a$ is H. In some embodiments, "d" is 6 or 7.

See WO 2008/017074, U.S. Ser. No. 12/376,243 (filed Feb. 3, 2009), and U.S. Ser. No. 12/376,225 (filed Feb. 3, 2009), each of which is incorporated herein by reference in its entirety, for a further description of suitable non-ionic oligomeric or polymeric solubilizing groups, and method for incorporating them into dyes.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Compounds of the invention can also include all isotopes of atoms occurring in the intermediates or final compounds. Isotopes include those atoms having the same atomic number but different mass numbers. For example, isotopes of hydrogen include tritium and deuterium.

The chemical substances represented herein by name, chemical formula, or structure are meant to include all stereoisomers, geometric isomers, tautomers, resonance structures, and isotopes of the same, unless otherwise specified.

The chemical substances described herein may be charged or include substituents with formal charges. When such chemical substances are represented as charged, it is understood that, unless otherwise specified, the charges are generally countered with an appropriate counterion. For example, chemical substances or functional groups having a charge of −I are understood to be countered with an ion have a +1 charge. Suitable counterions with +1 charge include Na+, K+, tetraalkylammonium ions, and the like. Conversely chemical substances or functional groups having a charge of +1 are understood to be countered with an ion having a −1 charge. Suitable counterions with −1 charge include F—, Cl—, Br—, I—, perchlorate, acetate, trifluoroacetate, and the like.

As used herein, the term "zwitterionic group," "zwitterionic ligand," or "zwitterion" refer to one or more charged moieties or ligands which are present on or can be reacted with a metal chelator core. The zwitterionic metal chelators of the claimed invention are decorated by one or more zwitterionic groups, i.e., moieties combining positive (A+, FIG. 3) and negative charges (B−, FIG. 3) that sum to a net charge of zero. These zwitterionic groups are distinct from metal chelator cores, which typically has negative charges to chelate positively-charged metals. For example, a zwitterionic metal chelator with a chelator core of −4 that binds a +4 metal would have a total net charge of zero. Although a total net charge of zero is considered ideal, a zwitterionic metal chelator with a chelator core of −4 that binds a +2 metal, resulting in an overall charge of −2, would still be expected to exhibit improved properties in vivo because of shielding of the chelator core/metal complex by one or more zwitterionic groups. In the absence of zwitterionic groups, the molecule would have no such shielding or expanded water of hydration and would be more likely to bind non-specifically.

A particular active agent molecule may have several attached "zwitterionic groups" or charge pairs. In general, the anion portion and the cation portion of the zwitterionic group (charge pair) will be part of the same moiety, though it is possible for two ionic groups to be used as separate moieties to form a zwitterionic group. In particular embodiments, the zwitterionic group is covalently bound to the base structure via a carbon-carbon bond, a carbon-oxygen bond, or a nitrogen-carbon bond. Examples of zwitterionic groups (charge pairs) that can be included in the compounds and complexes of the claimed invention include, but are not limited to, ammoniophosphates, ammoniophosphonates, ammoniophosphinates, ammoniosulfonates, ammoniosulfates, ammoniocarboxylates, ammoniosulfonamides, ammonio-sulfon-imides, guanidiniocarboxylates, pyridiniocarboxylates, pyridiniosulfonates, ammonio(alkoxy)dicyanoethenolates, ammonioboronates, sulfoniocarboxylates, phosphoniosulfonates, and phosphoniocarboxylates. The charged groups in these zwitterions can be separated by suitable spacer groups (C in FIG. 3) like linear or branched alkyl chains, aryl or heteroaryl moieties. In certain embodiments, the zwitterionic groups can be derivatives of amino acids, such as amino carboxylic acids, amino phosphonic acids, amino phosphinic acids or amino sulfonic acids, furthermore, aminoalkyl substituted sulfates or phosphates. Zwitterions can also be derivatives of betaines, such as carboxybetaines, sulfobetaines, sulfabetaines, phosphobetaines or phosphabetaines or N-oxides or derivatives of sulfamic acid. Particular examples of zwitterionic groups include ammonium sulfobetaines or N-oxides. A simple example of a zwitterionic group at physiological pH is the charge pair of a carboxylic acid (deprotonated at physiological pH) and an amine (protonated at physiological pH).

In some embodiments, the zwitterionic metal chelators of the invention can also comprise a targeting vector for an agricultural process, chemical process, disease, or tissue-specific epitope, such as the cyclic peptide cRGDyK (aka cRGD, FIG. 4) bound to one or more arms of the metal chelator. cRGD is a cyclic derivative of the tripeptide Arg-Gly-Asp which can be conjugated to one or more arms of the metal chelators of the invention. In still other embodiments, the targeting vector is octreotide or bombesin. In other embodiments, the targeting vector is KUE or dPSMA-617, a small molecule capable of targeting Fibroblast Activation Protein (FAP) also called FAP-inhibitor or FAPI, an amino acid or combination of amino acids, or derivatives thereof. In such embodiments, the targeting vector-conjugates can be formed in place of one or more zwitterionic groups. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

An ideal active agent conjugated to a targeting vector would adopt the total net charge of the targeting vector, which is purposeful because in most cases the charges on the targeting vector are crucial for the ability to bind its target. Targeted zwitterionic metal chelators thus retain the major advantage of minimizing non-specific binding while maximizing specific binding. It should be apparent to those skilled in the art that additional charges can be added to the zwitterionic metal chelator, if needed, to balance overall surface charge to zero.

In certain embodiments, the imaging agents or zwitterionic metal chelators of the combination compositions comprise a reactive linking group. Such reactive linking groups are typically an activated derivative of a carboxylic acid, such as an n-hydroxysuccinimide (NHS) ester, a sulfo-NHS ester, a pentafluorophenyl (PFP) ester, a hydroxybenzotriazole (HOBt) ester, a hydroxyazabenzotriazole (HOAt) ester, a tetrafluorophenyl (TFP) ester, an acid anhydride, an acid azide or an acid halide. Such reactive linking groups can be bound or substituted onto the chelator at any suitable structural location as would be understood by one of ordinary skill in the synthesis of such compounds. Reactive linking groups also include, but are not limited to, alkynes, azides, maleimides, thiols, amines, alcohols, phenols, carbonyls, phosphanes, alkenes and tetrazines.

Composition of Combinations of Imaging Agent Conjugates

In one aspect, the invention is directed to a composition having a combination of two or more imaging agent conjugates. Each of the imaging agent conjugates in the combination comprises a imaging agent conjugated to a targeting ligand. The imaging agent of the invention may include an imaging agent dye and/or a zwitterionic metal chelating agent In certain embodiments, the imaging agent has zwitterionic metal chelators coordinated to or labeled with a metal or metal isotope for detection, imaging, and treatment in a subject or in a biological sample. Non-limiting examples of metals that may be complexed with the chelators of the invention include Gd, Mn, Cu, Co, Y, In, Ga, Zr, Tc, Eu, Tb, Ac, Lu and other lanthanide or actinide metals. In some embodiments, the metals can be radioactive metal isotopes. Non-limiting examples of radioactive metal isotopes that may be used include Ga-66, Ga-67, Ga-68, Cu-64, Cu-67, Y-86, Co-55, Zr-89, Sr-83, Mn-52, As-72, Sc-44, Gd-153, Co-57, In-111, Zr-89, Ac-225, Tc-99m, or F-18 FDG.

In certain embodiments, the imaging agent includes one or more of ZW700-1-Forte, ZW800-1, ZW830-1, ZW-DOTA, ZW-PyC3A, ZW-Macropa, ZW-porphyrin, ZW-NOTA, and ZW-deferoxamine.

In certain embodiments, the targeting ligand includes one or more of a cRGD, a PSMA binding vector, such as dPSMA-617 or KUE, a FAP binding vector, a bombesin receptor binding vector, a somatostatin receptor binding vector, an octreotide vector, or any their dimers.

In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

In certain embodiments, the combination of the imaging agent conjugates includes two imaging agent conjugates. In certain embodiment, the combination of the imaging agent conjugates includes three imaging agent conjugates. In certain embodiment, the combination of the imaging agent conjugates includes four imaging agent conjugates.

In certain embodiments, each of the imaging agent conjugates in the combination of the composition has the same imaging agent conjugated to different targeting ligands. In certain embodiments, each of the imaging agent conjugates in the combination has the same targeting ligand conjugated to different imaging agents. In certain embodiment, each of the imaging agent conjugates in the combination has the imaging agent and the targeting ligand different from the others in the combination.

For the disclosed methods of detecting/imaging benign or malignant tissues, any metal isotope known to emit radiation in a form that is readily detectable by conventional imaging means can be incorporated into the targeting backbone. Non-limiting examples of "conventional imaging means" include gamma ray detection, PET scanning, SPECT scanning, and MRT scanning. Non-limiting examples of metals that may be complexed with the chelators of the imaging agent of the invention include Gd, Mn, Cu, Co, Y, In, Ga, Zr, Tc, Eu, Tb, Ac, Lu and other lanthanide or actinide metals. In some embodiments, the metals can be radioactive metal isotopes. Non-limiting examples of radioactive metal isotopes that may be used include Ga-66, Ga-67, Ga-68, Cu-64, Cu-67, Y-86, Co-55, Sr-83, Mn-52, As-72, Sc-44, Gd-153, Co-57, In-111, Zr-89, Ac-225, or Tc-99m.

For the disclosed methods of therapeutically treating malignant tumors, any radioactive metal isotope known to emit ionizing radiation in a form that would result in the death of cells that take up the analogs labeled with the radioactive metal isotope can be incorporated by chelation in the zwitterionic metal chelators of the invention. So, too, can non-radioactive metals that are capable of capturing neutrons and releasing cytotoxic radiation (neutron capture therapy). In some embodiments, the radioactive metal isotope emits its ionizing radiation in a form that minimizes damage to tissue outside of the cells that take up the labeled analogs. In certain embodiments, the invention provides combinations of imaging agent conjugates having imaging agents comprising one or more radioisotope suitable for use in radiation therapy. In certain embodiments, the imaging agent conjugates of the invention comprise zwitterionic metal chelators, which comprise at least one radioactive isotope of technetium, rhenium, gallium, indium, copper, yttrium, actinium, bismuth, samarium, dysprosium, holmium, or lutetium, including radioactive isotopes selected from Tc-99m, Tc-94m, Re-186, Re-188, Ga-68, Cu-64, Cu-67, Y-90, Y-86, Ac-225, Bi-213, In-111, Sm-153, Ho-166, Lu-177, Sc-43, Sc-44, Sc-47, Tb-149, Tb-152, Tb-155, Tb-161, and Dy-166. In other embodiments, non-limiting examples of metals used in neutron capture therapy include Zr-88 or Gd-157.

In certain embodiments, when selecting a combination of the imaging agent conjugates, half-life of the radioactive metal isotopes of the zwitterionic metal chelators is considered. Selection of other combinations can be determined based on the half-life of radioactive metal isotopes Ga-66, Ga-67, Ga-68, Cu-64, Cu-67, Y-86, Co-55, Zr-89, Sr-83, Mn-52, As-72, Sc-44, Gd-153, Co-57, In-111, Zr-89, Ac-225, Tc-99m, or F-18 FDG. In certain embodiments, a combination of the imaging agent conjugates having radioactive metal isotopes of various half-life is desired. For example, a combination of an imaging agent conjugate having F-18 FDG, which has a short half-life, as its radioactive metal isotope and an imaging agent conjugate having Cu-64 or Zr-89, which has a long half-life, as its radioactive metal isotope is desired.

Imaging Agents and Metal Chelators

ZW700-1 Forte

ZW700-1 Forte is a 700-nm zwitterionic pentamethine indocyanine near-infrared fluorophore which permits dualchannel image-guided surgery. In certain embodiments, the charge-balanced imaging agent is ZW700-1 Forte having the formula:

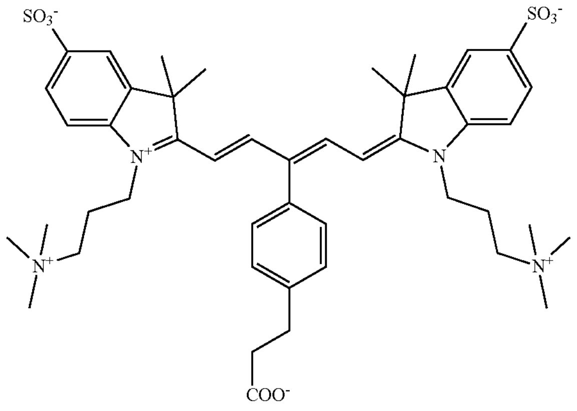

ZW-700-1c
ZW-700-1-Forte

Scheme 1

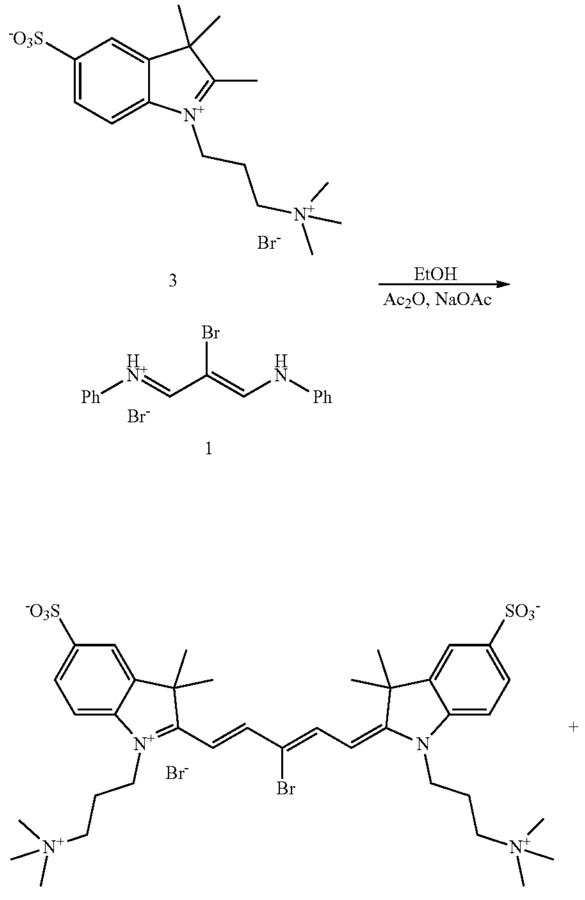

3

1

5

-continued

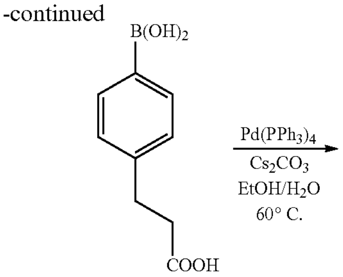

ZW800-1

ZW800-1 is a 800-nm zwitterionic near-infrared fluorophore. In certain embodiments, the charge-balanced imaging agent is ZW800-1 having the formula:

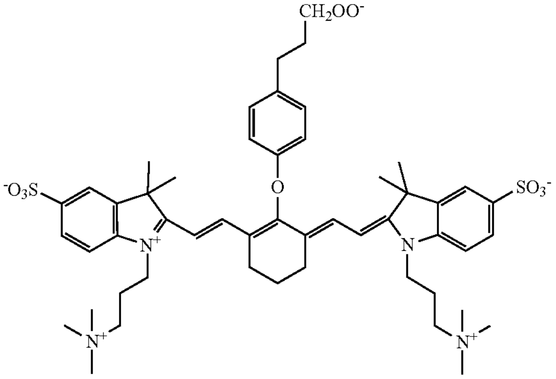

ZW830-1

ZW800-1 is a 830-nm zwitterionic near-infrared fluorophore. In certain embodiments, the charge-balanced imaging agent is ZW830-1 having the formula:

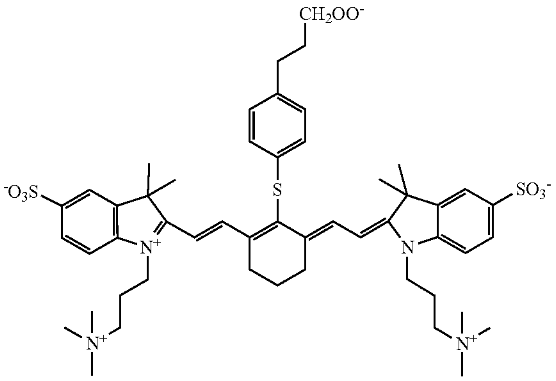

ZW-DOTA

In certain embodiments, the ZW-DOTA includes the one of the following formulas:

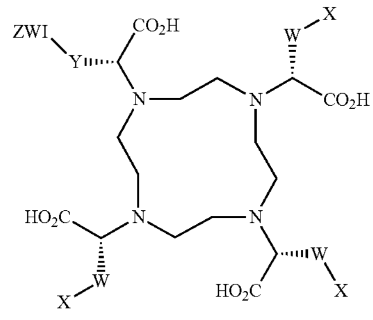

or

ZWI-DOTA-$X_3$

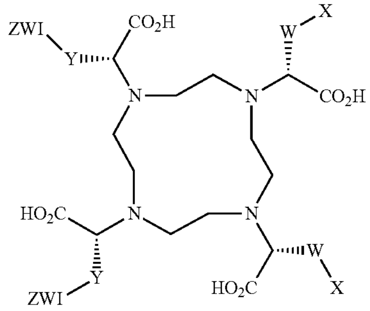

or 1,4-$(ZWI)_2$-DOTA-$X_2$

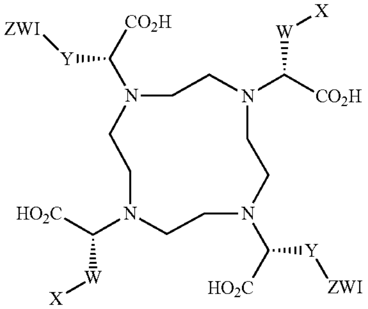

1,7-$(ZWI)_2$-DOTA-$X_2$

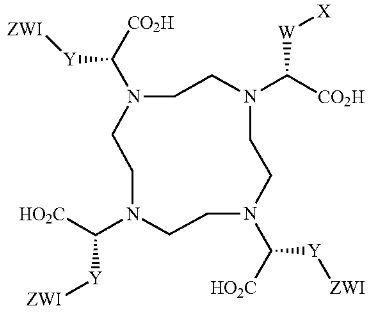

or $(ZWI)_3$-DOTA-X

-continued

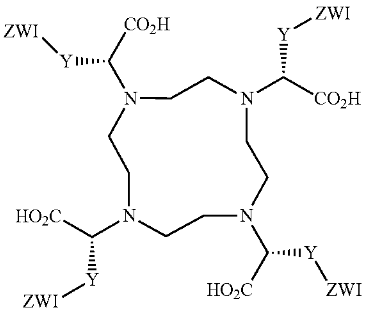

$(ZWI)_4$-DOTA in which ZWI represents a zwitterionic group; each instance of W and Y independently represent a linking group, and each instance of X represents a reactive group. In certain embodiments, ZWI represents an ammonium sulfobetaine group.

In such embodiments, a ZW-DOTA contains stereogenic centers, any of these might have R or S-configuration. The ZW-DOTA might be a single stereoisomer or might be a mixture of stereoisomers. The ZW-DOTA includes 1, 2, 3, or 4 zwitterionic groups as defined in FIG. 3 and 1, 2 or 3 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In particular embodiments, the ZW-DOTA includes 1, 2, 3, or 4 zwitterionic groups and 4 carboxylate groups for complexation to the metal or metal isotope. In still other embodiments, the ZW-DOTA includes 1, 2, 3, or 4 zwitterionic groups, 4 carboxylate groups for complexation to the metal or metal isotope, and one or more targeting vectors. These targeting vectors can be bound to the chelator at any suitable structural location (e.g. reactive group X) as would be understood by one of ordinary skill in the synthesis of such compounds.

Such ZW-DOTA can be synthesized using the protocol described in Scheme 2.

Scheme 2

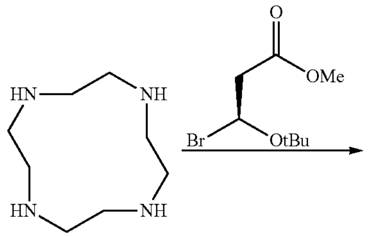

-continued

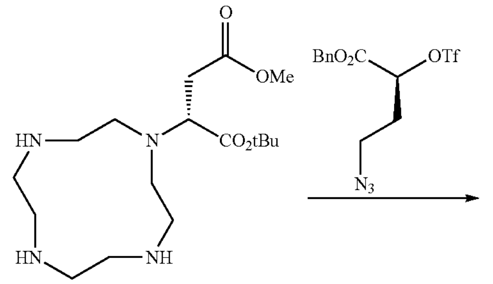

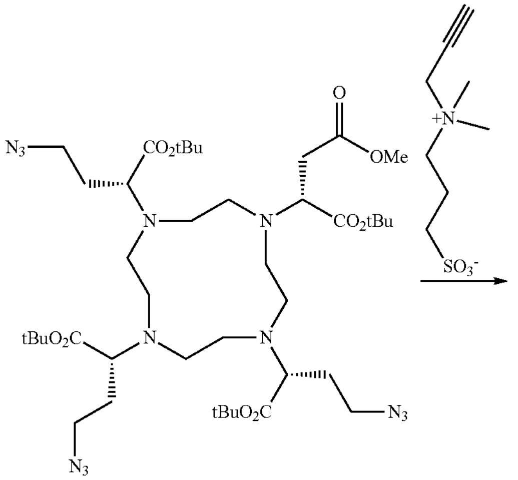

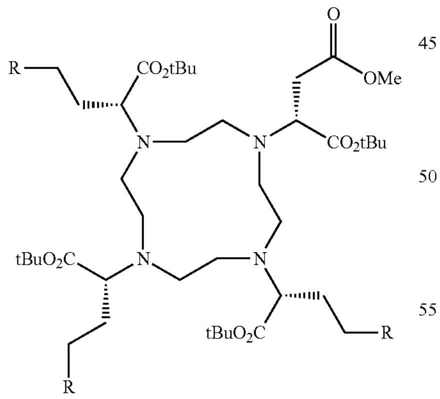

orthogonally protected
$(ZWI)_3$-DOTA-$CO_2Me$

-continued

R =

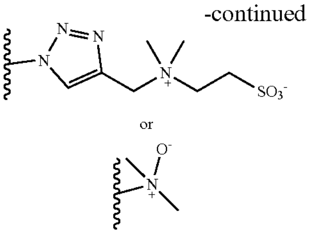

or

In a particular embodiment, the ZW-DOTAs can be complexed with Zr, Cu, Ga, In, Y, Gd, Lu, Tb or other metals.

In still other embodiments, one or more zwitterionic groups of the ZW-DOTA can be replaced with a targeting vector, such as cRGD, dPSMA-617, KUE, a FAP-targeting small molecule, octreotide, bombesin, octreotide or their corresponding homo- or hetero-dimers provided that ZW-DOTA remains the imaging agent. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

Figure 5:
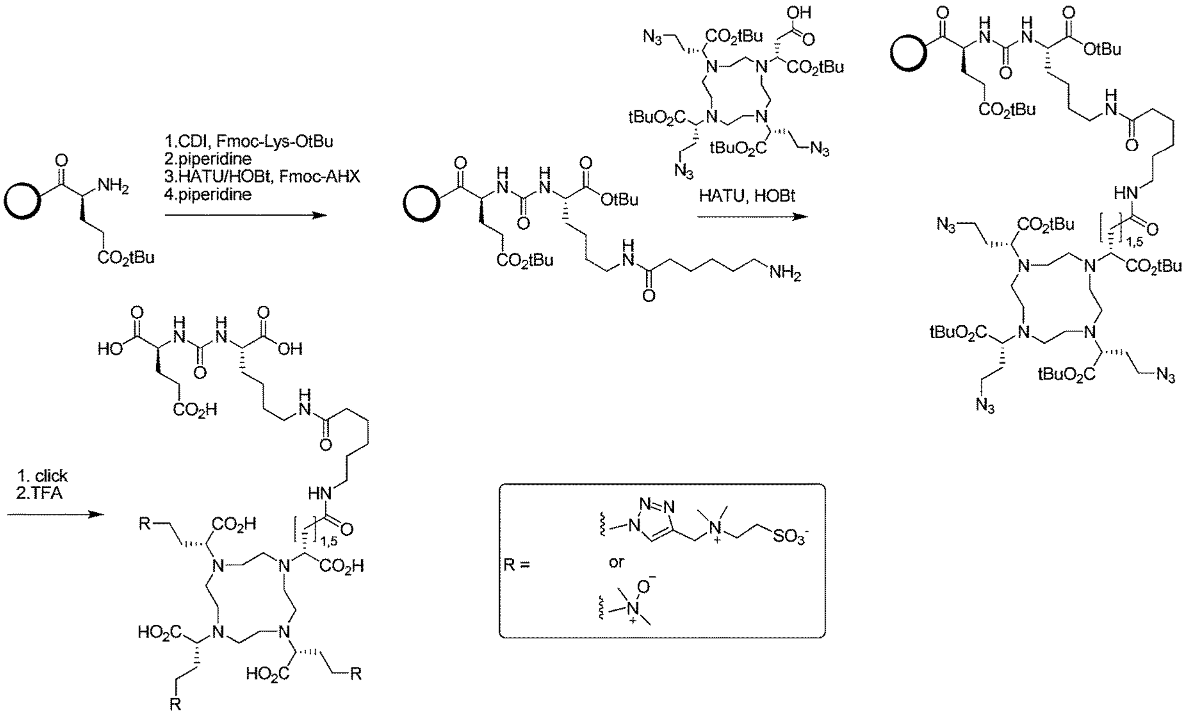
FIG. 5 is a representation of the synthesis of ZW-DOTA (Scheme 2)

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 5. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

In certain embodiments, the agent further comprises a PEG-moiety to alter the circulation time in blood. Such moiety can be bound to the conjugate at any suitable structural location as would be understood by one of ordinary skill in the synthesis of such compounds.

In certain embodiments, the conjugate of the ZW-DOTA and the targeting vector has the following formula with KUE, dPSMA-617, cRGD, FAPI, octreotide, bombesin, or octreotide as the targeting vector (tv):

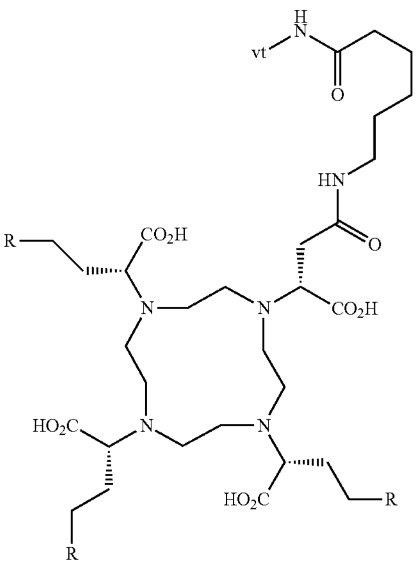

(ZWI)$_3$-DOTA-AHX-tv

-continued

R = 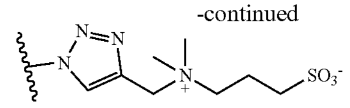 or

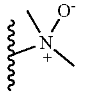

In certain embodiments, the targeting ligand includes one or more of LyP-1 peptide having a sequence of CGQKR-TRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

Such DOTA-based zwitterionic conjugates can be synthesized using the protocol described in Scheme 2 (shown in FIG. 5)

In certain embodiments, the ZW-DOTA is not ZWI3-DOTA-Ahx-cRGD.

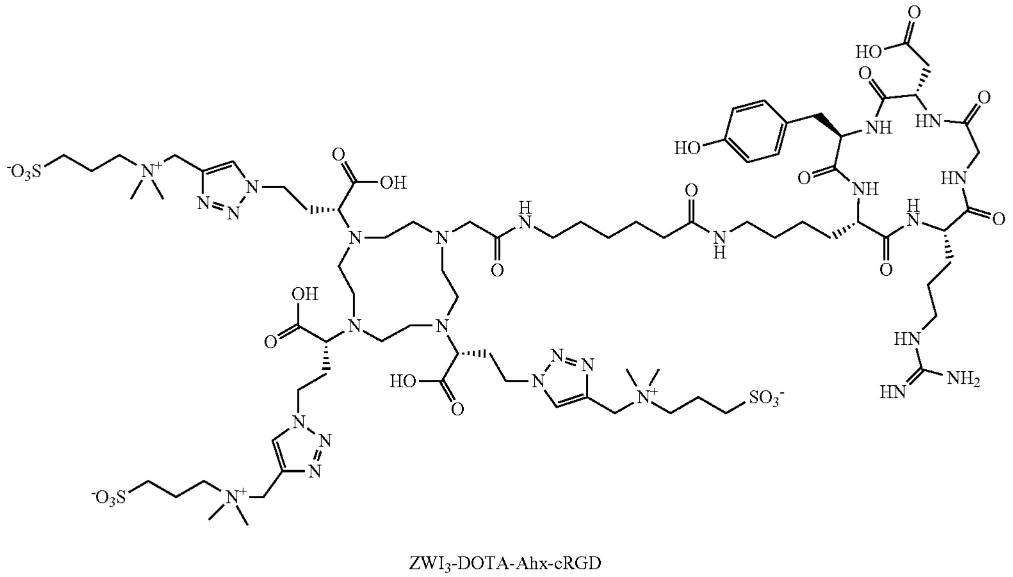

ZWI$_3$-DOTA-Ahx-cRGD

In certain embodiments, the ZW-DOTA is not:
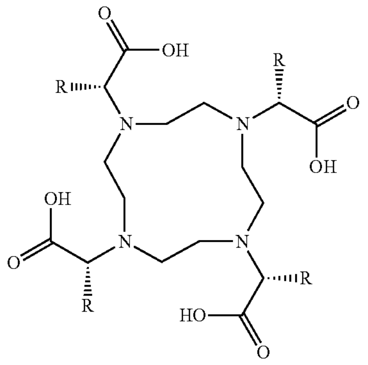
wherein
R =
triazol-ZWI =
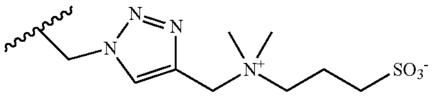
triazol-Sulfo =
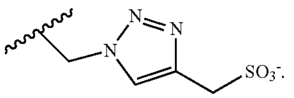
triazol-Kat =
ZW-PyC3A
In certain embodiments, the ZW-PyC3A includes the one of the following formulas:
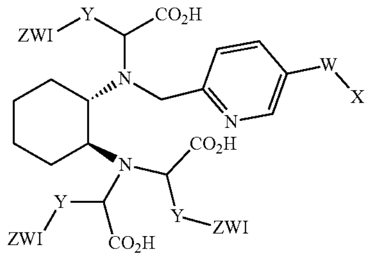
(ZWI)$_3$-PyC$_3$A-X
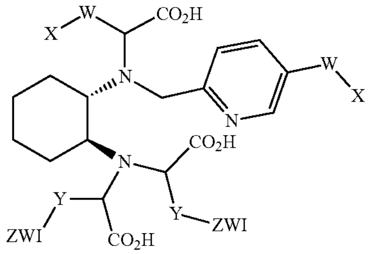
(ZWI)$_2$-PyC$_3$A-X$_2$
In certain embodiments, the ZW-DOTA is not:
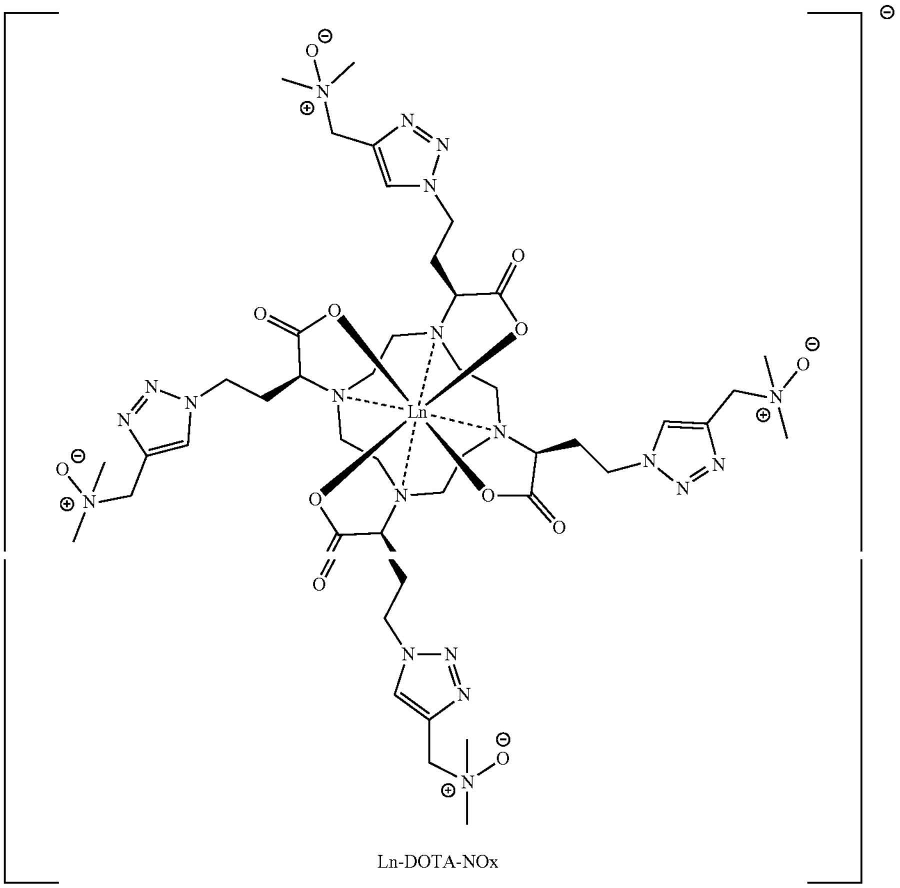
Ln-DOTA-NOx -continued

V1

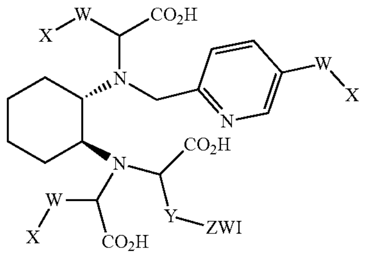

ZWI-PyC$_3$A-X$_3$

V2

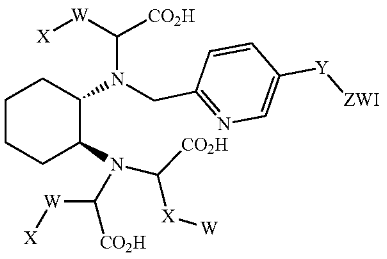

ZWI-PyC$_3$A-X$_3$

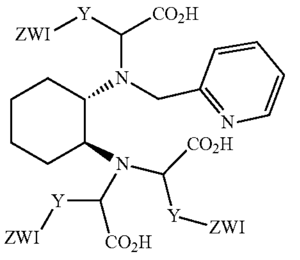

(ZWI)$_3$-PyC$_3$A

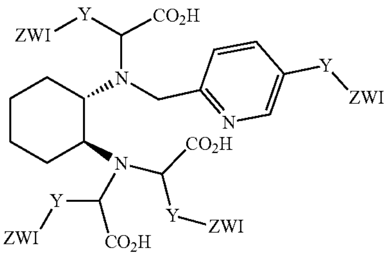

(ZWI)$_4$-PyC$_3$A wherein each of W and Y may independently be absent. In certain embodiments, ZWI represents an ammonium sulfobetaine group.

Figure 2:
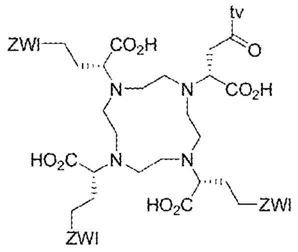
FIG. 2 is a representation of seven imaging conjugates with zwitterionic metal chelators as the imaging agent according to the invention (targeting vector/ligand=tv).
Figure 2:
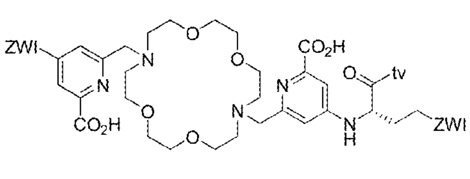
Figure 2:
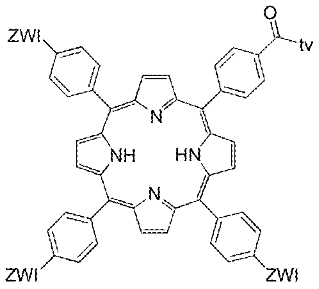
Figure 2:
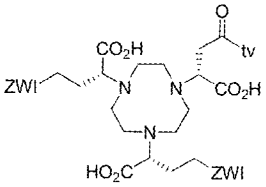
Figure 2:
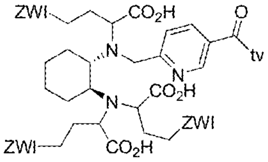
Figure 2:
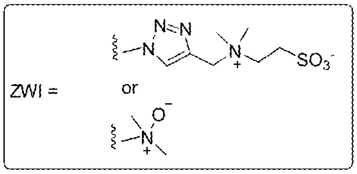
Figure 2:
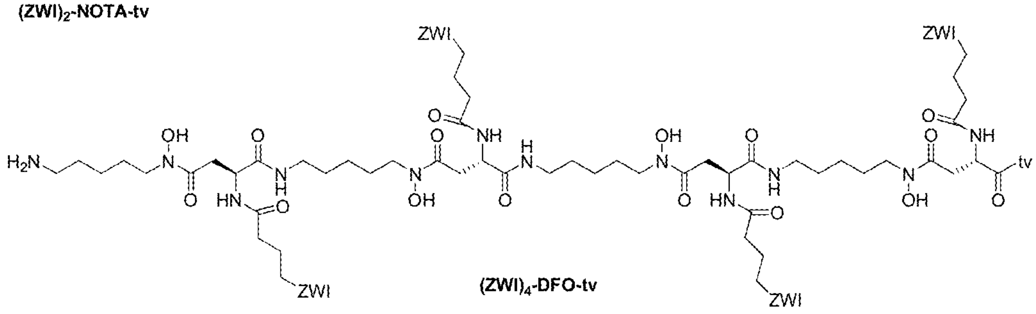
Figure 3:
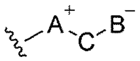
FIG. 3. is a representation of Zwitterionic groups as the imaging agent of an imaging conjugate according to the invention.
Figure 3:
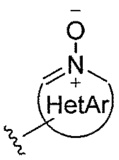

In such embodiments, a ZW-PyC3A includes 1, 2 3 or 4, zwitterionic groups as defined in FIG. 3 and 1, 2 or 3 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In certain embodiments, ZWI represents an ammonium sulfobetaine group.

Such ZW-PyC3A can be synthesized using the protocol described in Scheme 3.

Scheme 3

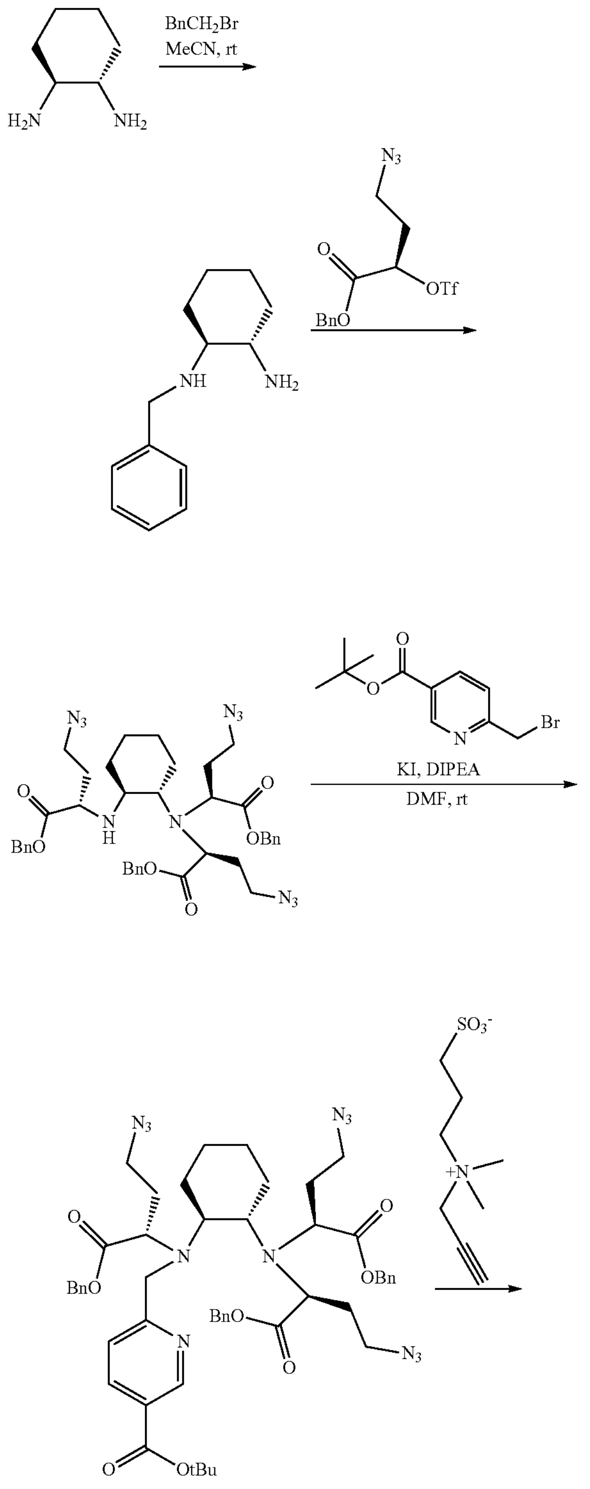

-continued

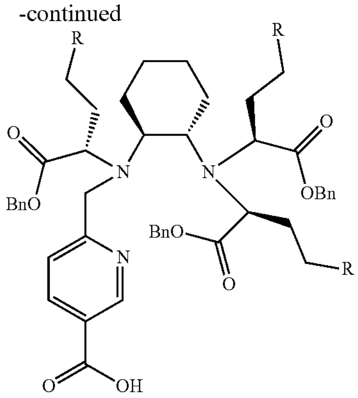

protected $(ZWI)_3$-$PyC_3A$-$CO_2H$

R = 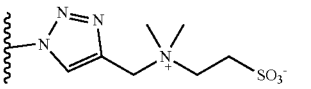 or 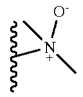

In particular embodiment, the ZW-PyC3A can be complexed with Mn or similar metals.

In still other embodiments, one or more zwitterionic groups of the ZW-PyC3A can be replaced with a targeting vector, such as cRGD, dPSMA-617, FAPI, octreotide, bombesin, octreotide or corresponding homo- or heterodimers provided that PyC3A-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown below:

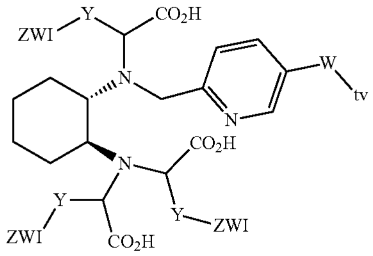

$(ZWI)_3$-$PyC_3A$-tv

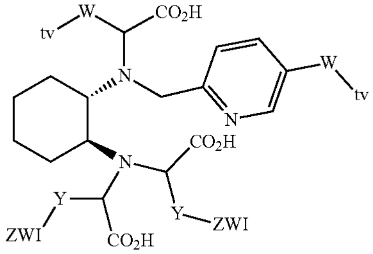

$(ZWI)_2$-$PyC_3A$-$(tv)_2$

V1

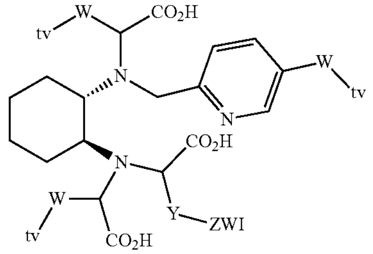

ZWI-$PyC_3A$-$(tv)_3$

V2

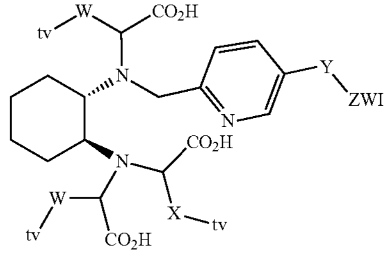

ZWI-$PyC_3A$-$(tv)_3$ V2

The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety.

In certain embodiments, the agent further comprises a PEG-moiety to alter the circulation time in blood. Such moiety can be bound to the conjugate at any suitable structural location as would be understood by one of ordinary skill in the synthesis of such compounds.

ZW-Macropa

In certain embodiments, the ZW-Macropa includes the one of the following formulas:

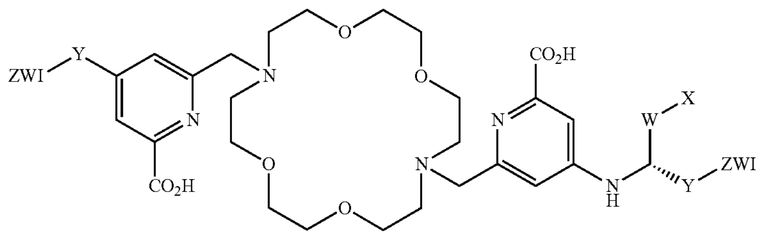

(ZWI)$_2$-macropa-X

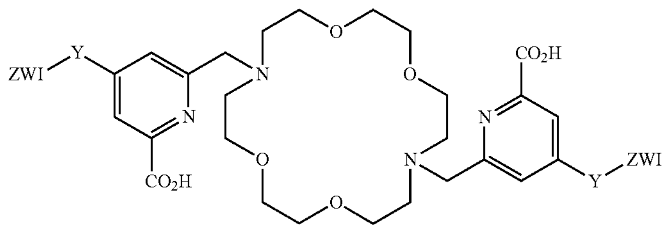

(ZWI)$_2$-macropa

V1

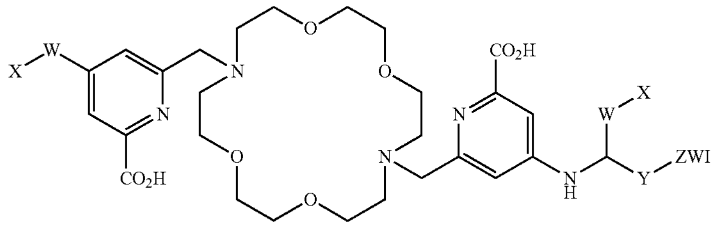

ZWI-macropa-X$_2$

V2

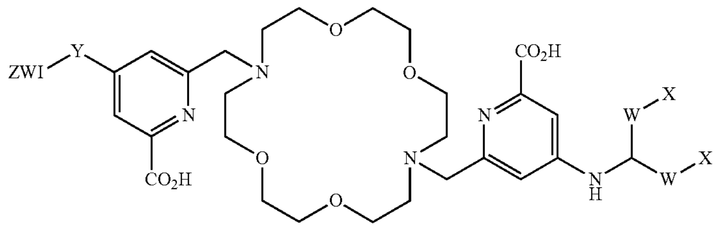

ZWI-macropa-X$_2$ wherein ZW represents a zwitterionic group.

In such embodiments, a ZW-Macropa includes 1 or 2 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. Such ZW-Macropa can be synthesized using the protocol described in Scheme 4.

Scheme 4

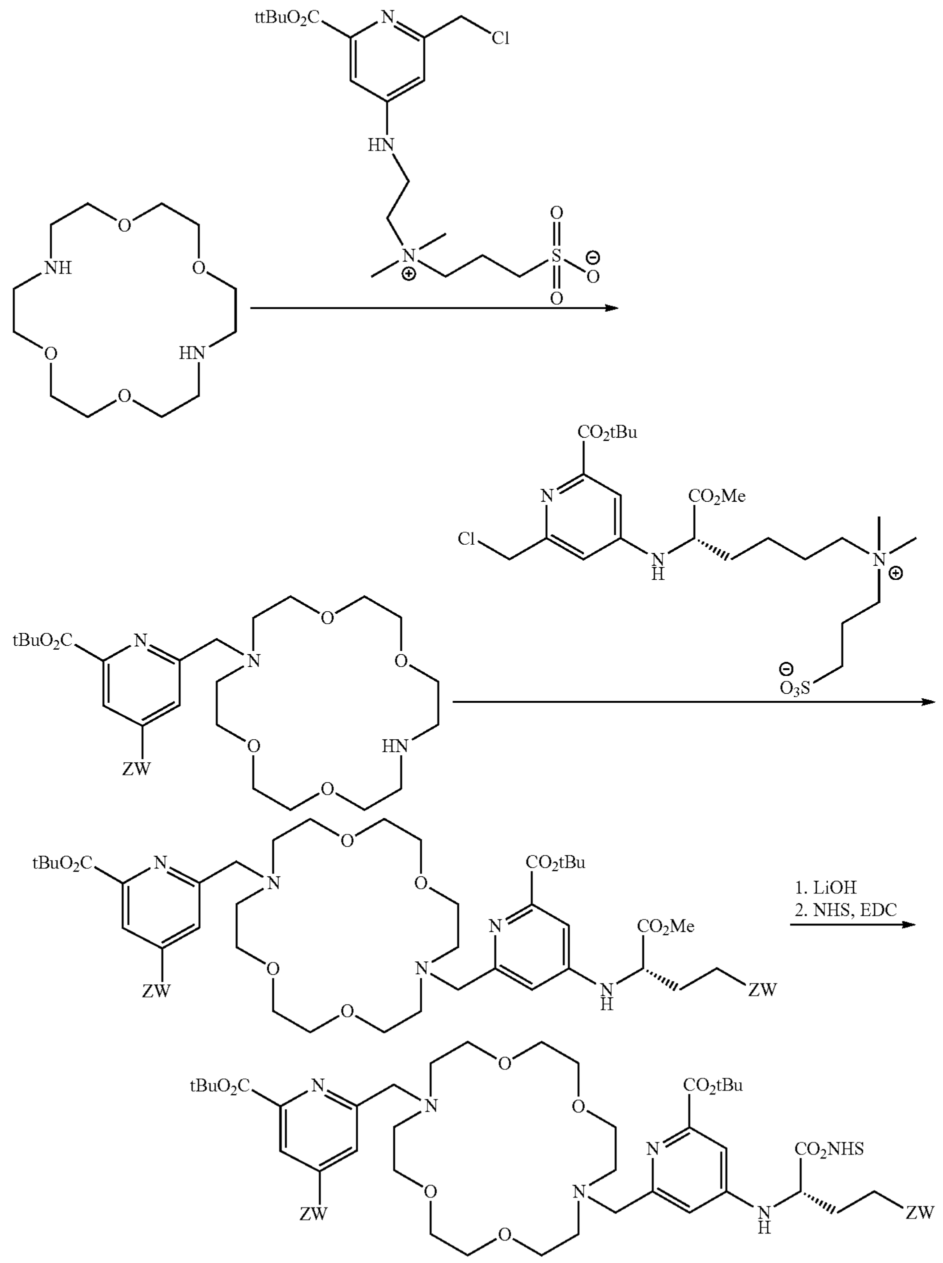

In a particular embodiment, the ZW-Macropa can be complexed with $Ac^{3+}$, $Bi^{3+}$, or similar metal cations.

In still other embodiments, one or more zwitterionic groups of the macropa-based zwitterionic metal chelator can be replaced with a targeting vector, such as cRGD, dPSMA-617, KUE, a FAP-targeting small molecule, octreotide, bombesin, octreotide, or their corresponding homo- or heterodimers, provided that macropa-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 7. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of ZW-Macropa and targeting vectors (tv) include, but are not limited to:

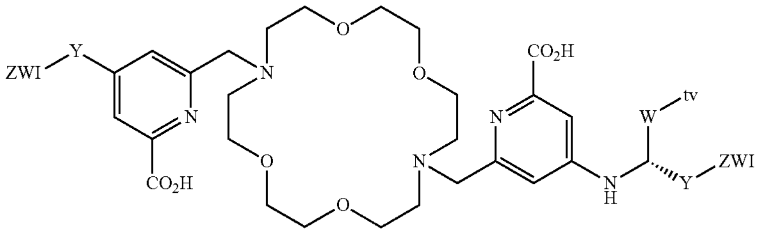

(ZWI)$_2$-macropa-tv

V1

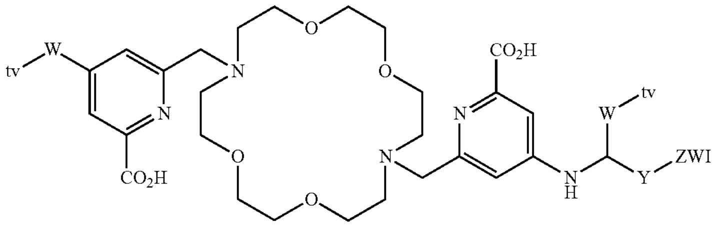

ZWI-macropa-tv$_2$

V2

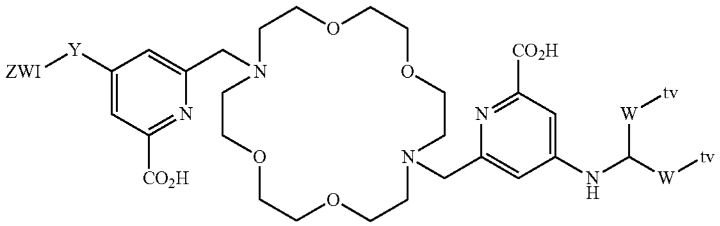

ZWI-macropa-tv$_2$

In certain embodiments, the agent further comprises a PEG-moiety to alter the circulation time in blood. Such moiety can be bound to the conjugate at any suitable structural location as would be understood by one of ordinary skill in the synthesis of such compounds.

ZW-Porphyrin

In certain embodiments, the ZW-porphyrin includes the one of the following formulas:

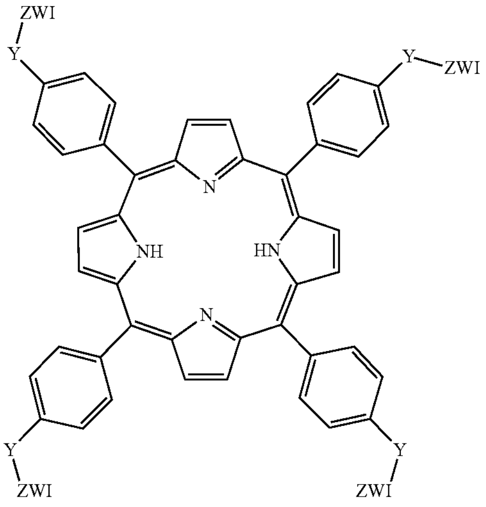

(ZWI)4-porphyrin

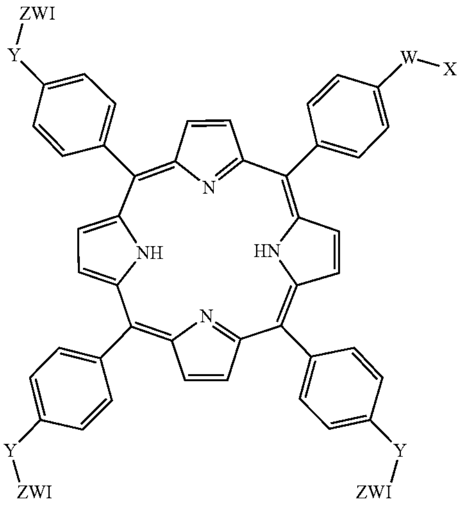

(ZWI)3-porphyrin-X

-continued

V1

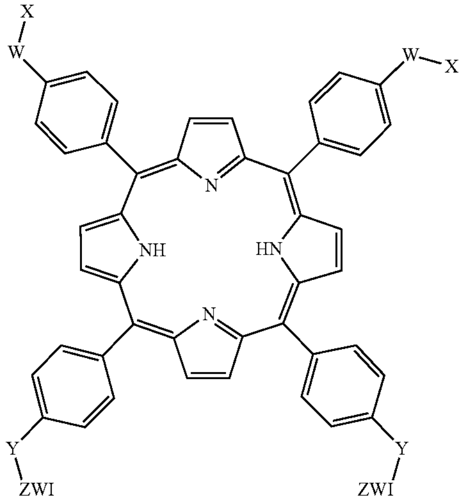

(ZWI)2-porphyrin-X2

V2

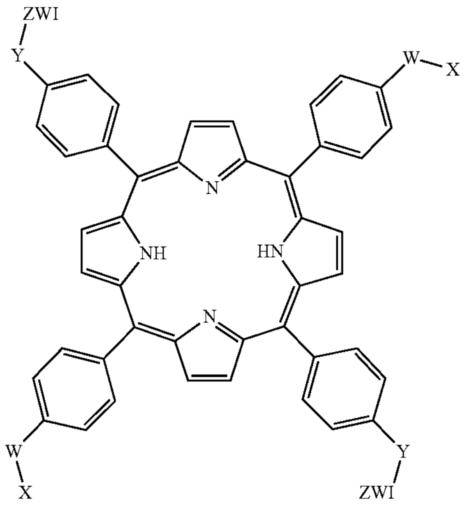

(ZWI)2-porphyrin-X2

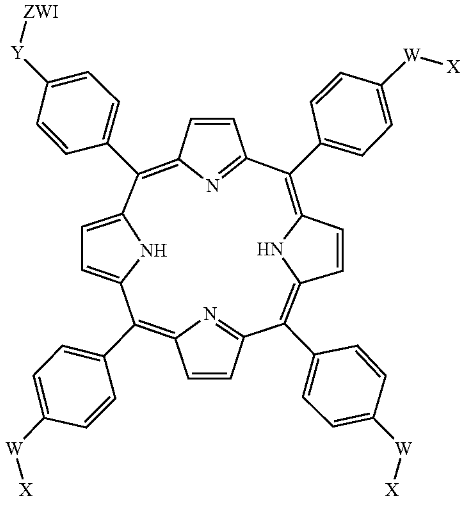

ZWI-porphyrin-X3 wherein ZW represents a zwitterionic group. In certain embodiments, ZW represents an ammonium sulfobetaine group.

In such embodiments, a ZW-Porphyrin includes 1, 2, 3, or 4 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In particular embodiments, the ZW-Porphyrin includes 4 zwitterionic groups. In certain embodiments, ZWI represents an ammonium sulfobetaine group.

In certain embodiments, the chelator comprises a reactive linking group, typically an activated derivative of a carboxylic acid, such as an NHS ester, a sulfo-NHS ester, a PFP ester, a HOBt ester, a HOAt ester, a TFP ester, an acid anhydride, an acid azide or an acid halide. Such reactive linking groups can be bound or substituted onto the chelator at any suitable structural location as would be understood by one of ordinary skill in the synthesis of such compounds.

In particular embodiments, the ZW-Porphyrin has the formula:

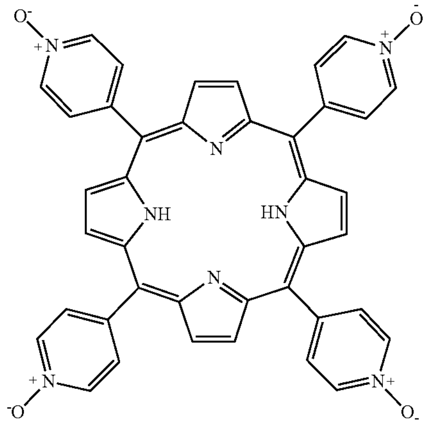

$(NOx)_4$-porphyrin

-continued

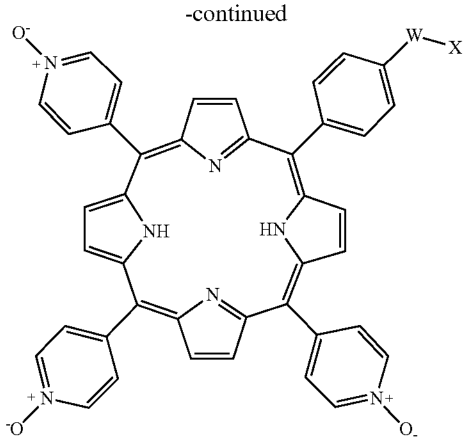

$(NOx)_3$-porphyrin-X

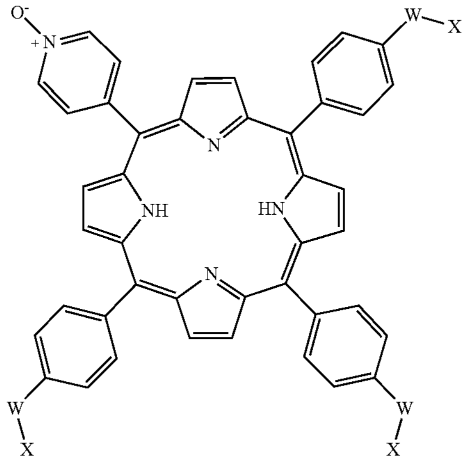

NOx-porphyrin-$X_3$ wherein the zwitterion is a pyridine-N-oxide (as drawn above) or an aromatic N-oxide derived from imidazole, pyrimidine or a similar heteroaromatic residue. X is a reactive group for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The reactive group X can be separated from the chelator core structure by appropriate spacer moieties W including alkyl, aryl or heteroaryl groups. In certain embodiments, each of W and Y may independently be absent.

ZW-Porphyrins can be synthesized using the protocol described in Scheme 5.

Scheme 5
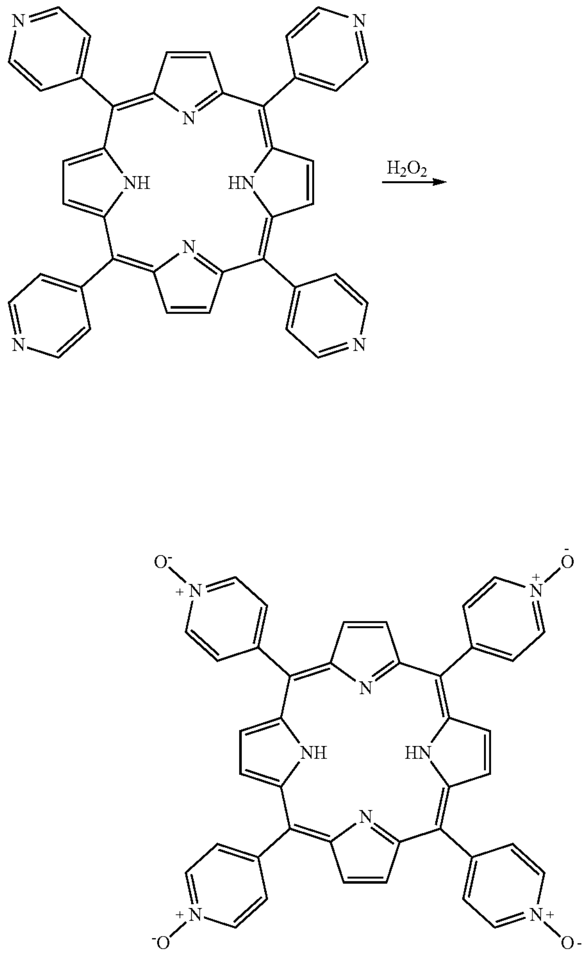
(NOx)$_4$-porphyrin
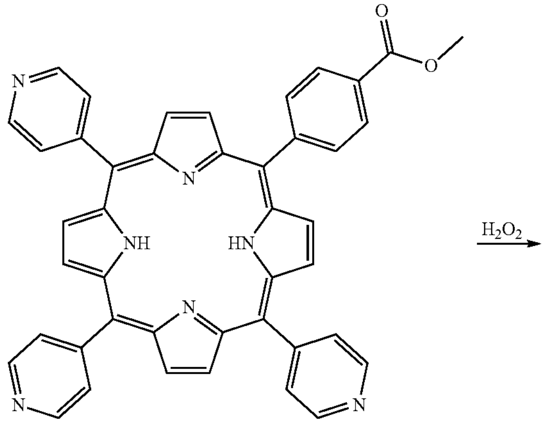
-continued
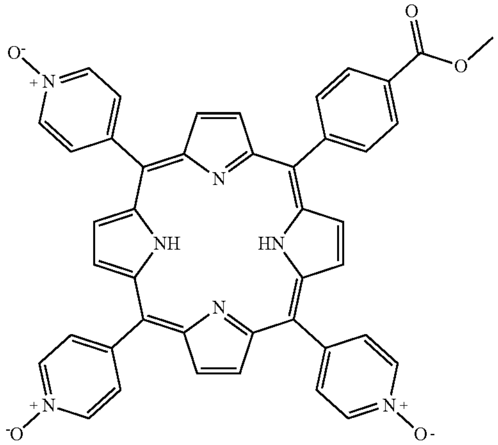
(NOx)$_3$-porphyrin-$CO_2Me$
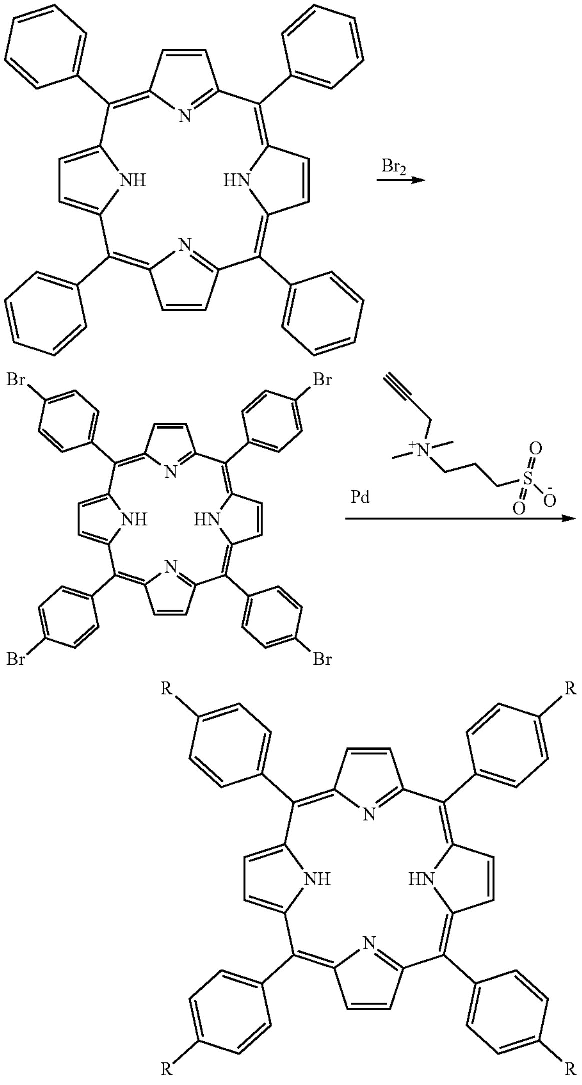
(ZWI)$_4$-porphyrin -continued R =
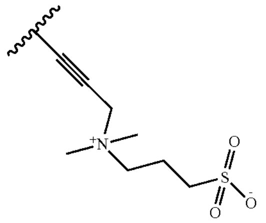

In a particular embodiment, the porphyrin-based zwitterionic metal chelators can be complexed with $Mn^{2+}$, $Mn^{3+}$, $Fe^{2+}$, $Fe^{3+}$, $Gd^{3+}$, $Ac^{3+}$, $Bi^{3+}$, or similar metal cations.

In still other embodiments, one or more zwitterionic groups of the porphyrin-based zwitterionic metal chelator can be replaced with a targeting vector, such as cRGD, dPSMA-617, KUE, a FAP-targeting small molecule, octreotide, bombesin, octreotide, or their corresponding homo- or heterodimers, provided that ZW-Porphyrin remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 8. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of porphyrin-based zwitterionic chelators and targeting vectors (tv) include, but are not limited to:

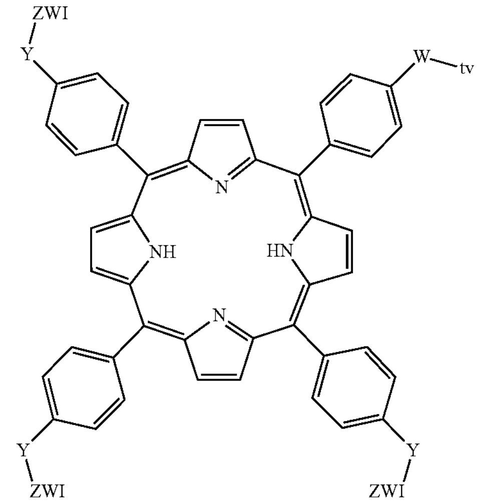

$(ZWI)_3$-porphyrin-tv

V1

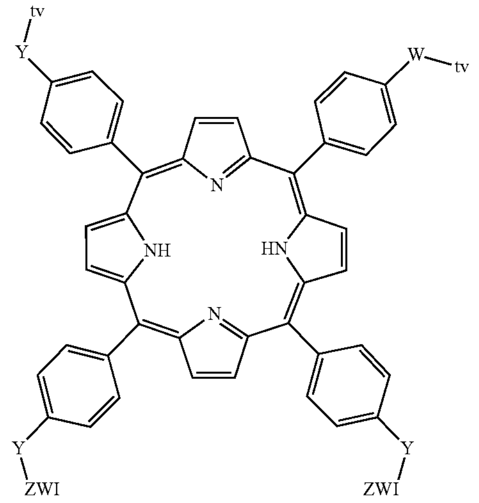

$(ZWI)_2$-porphyrin-$(tv)_2$

V2

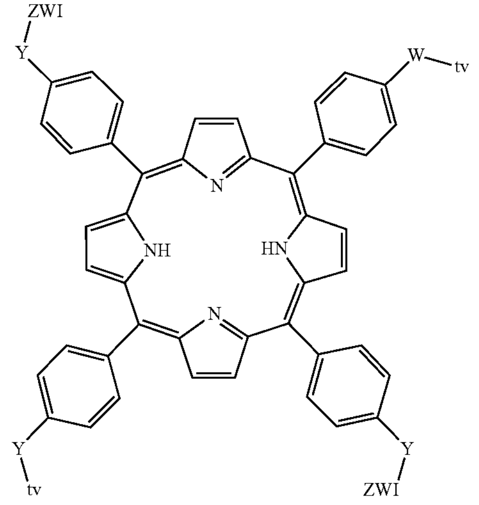

$(ZWI)_2$-porphyrin-$(tv)_2$

-continued

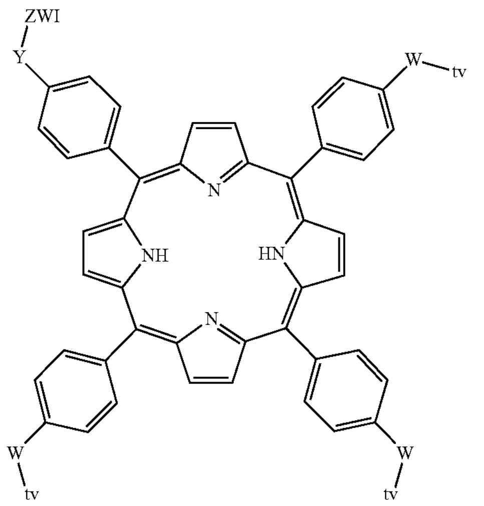

(ZWI)-porphyrin-$(tv)_3$

In certain embodiments, the ZW-Porphyrin has the formula:

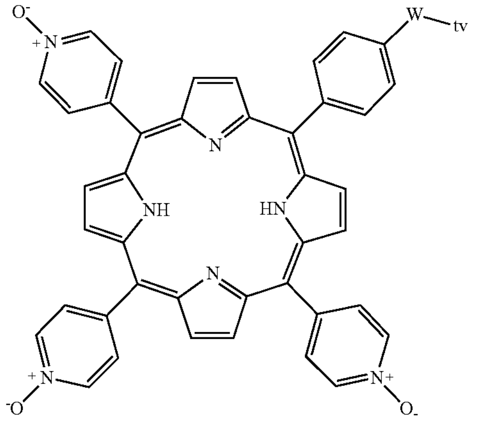

$(NOx)_3$-porphyrin-tv

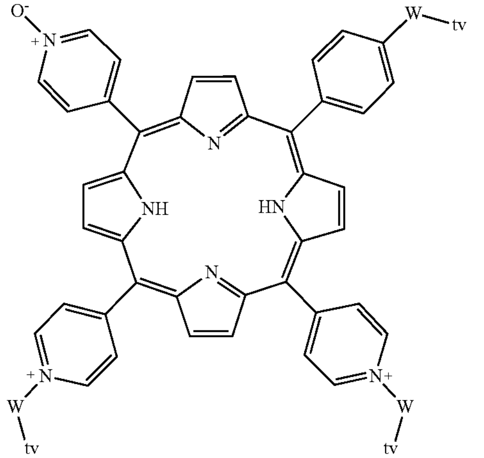

NOx-porphyrin-$(tv)_3$ wherein the zwitterion is a pyridine-N-oxide (as drawn above) or an aromatic N-oxide derived from imidazole, pyrimidine or a similar heteroaromatic residue.

In certain embodiments, the agent further comprises a PEG-moiety to alter the circulation time in blood. Such moiety can be bound to the conjugate at any suitable structural location as would be understood by one of ordinary skill in the synthesis of such compounds.

ZW-NOTA

In certain embodiments, the ZW-NOTA includes one of the following formulas:

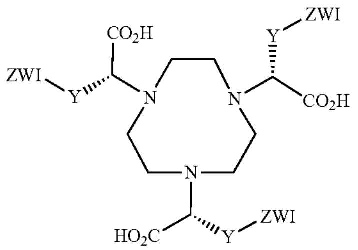

$(ZWI)_3$-NOTA

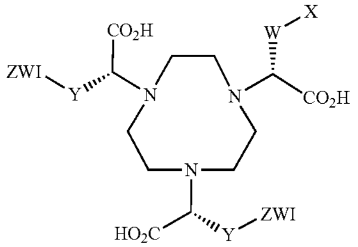

$(ZWI)_2$-NOTA-X

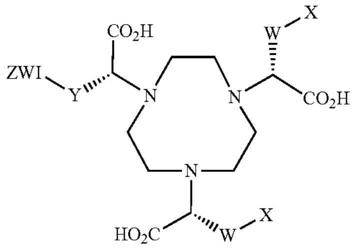

ZWI-NOTA-$X_2$

In such embodiments, a NOTA-based zwitterionic metal chelator includes 1, 2 or 3 zwitterionic groups. In particular embodiments, the NOTA-based zwitterionic metal chelator includes 2 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent.

In particular embodiments, the NOTA-based zwitterionic metal chelator has the formula:

Such NOTA-based zwitterionic metal chelators can be synthesized using the protocol described in Scheme 6.

Scheme 6

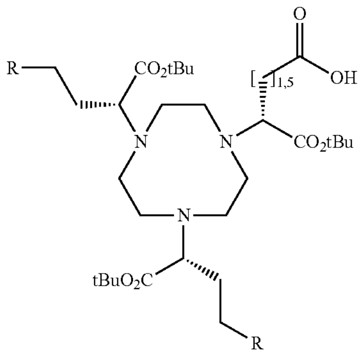

protected $(ZWI)_2$-NOTA-$CO_2H$

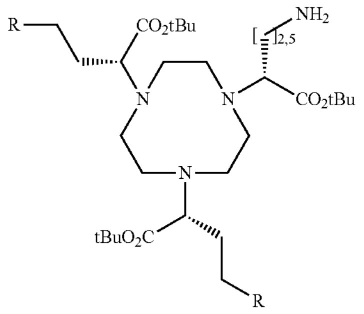

protected $(ZWI)_2$-NOTA-$NH_2$

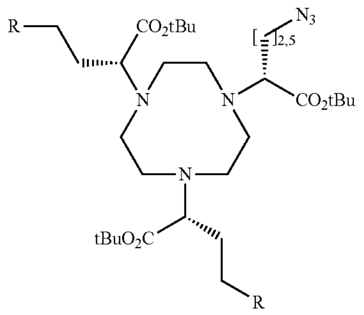

protected $(ZWI)_2$-NOTA-$N_3$

R =

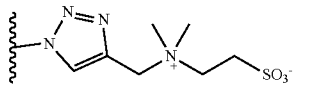

or

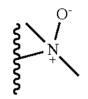

In a particular embodiment, the NOTA-based zwitterionic metal chelators can be complexed with $Ga^{3+}$, $Cu^{2+}$, $Gd^{3+}$, $Ac^{3+}$, $Bi^{3+}$, or similar metal cations.

In still other embodiments, one or more zwitterionic groups of the NOTA-based zwitterionic metal chelator can be replaced with a targeting vector, such as cRGD, dPSMA-617, KUE, a FAP-targeting small molecule, octreotide, bombesin, octreotide, or their corresponding homo- and heterodimers, provided that NOTA-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alkoxy derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 9. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of ZW-NOTA and targeting vectors (tv) include, but are not limited to:

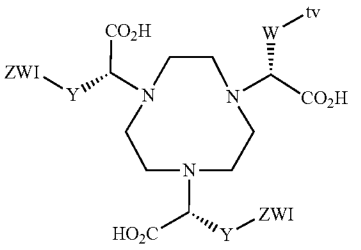

$(ZWI)_2$-NOTA-tv

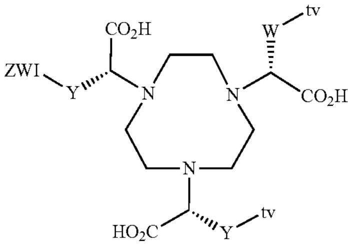

ZWI-NOTA-$(tv)_2$

In certain embodiments, the agent further comprises a PEG-moiety to alter the circulation time in blood. Such moiety can be bound to the conjugate at any suitable structural location as would be understood by one of ordinary skill in the synthesis of such compounds.

ZW-Deferoxamine
In certain embodiments, the ZW-deferoxamine has the formula:
V1
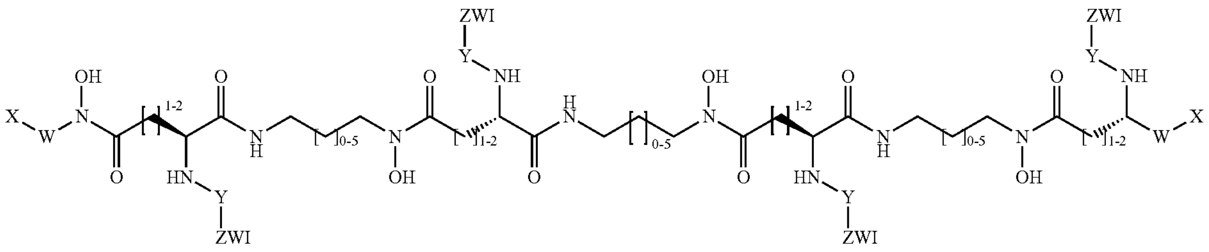
$(ZWI)_4$-DFO*-$X_2$
V1a
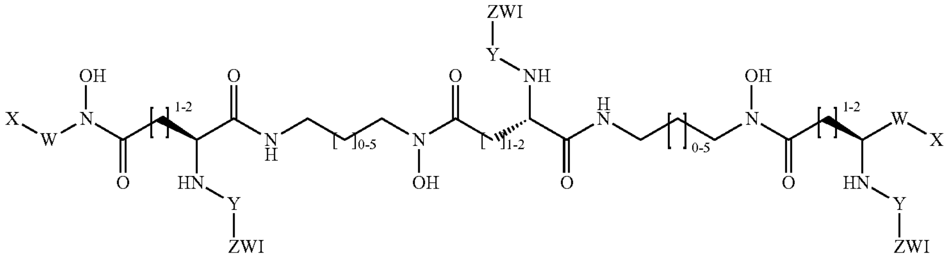
$(ZWI)_3$-DFO-$X_2$
V1b
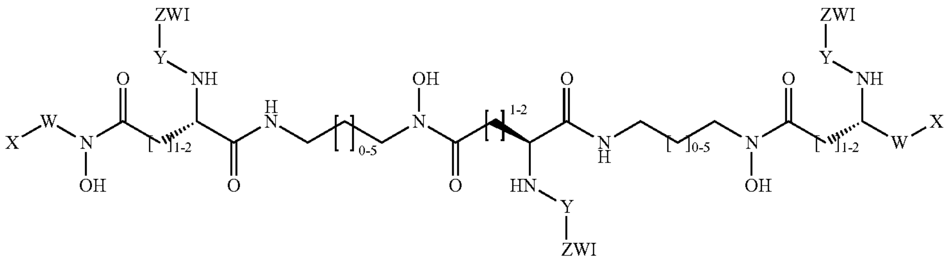
$(ZWI)_3$-DFO-$X_2$
V2
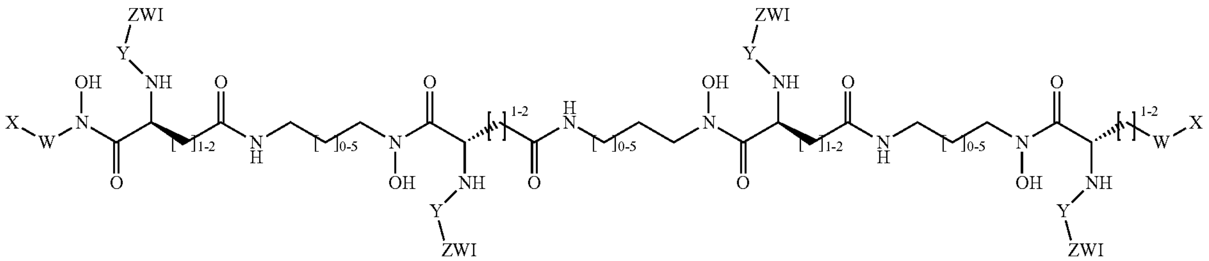
$(ZWI)_4$-DFO*-$X_2$ -continued
V2a
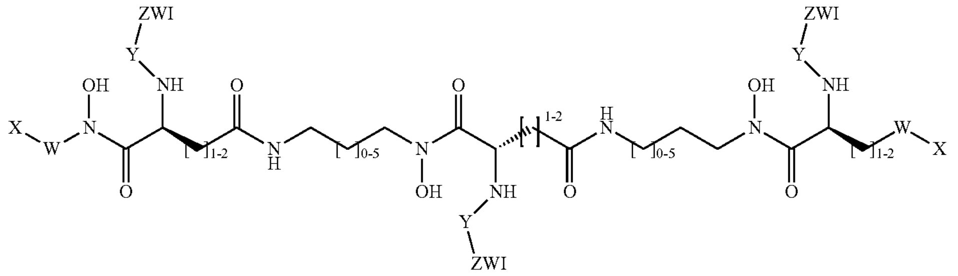
$(ZWI)_3$-DFO-$X_2$
V2b
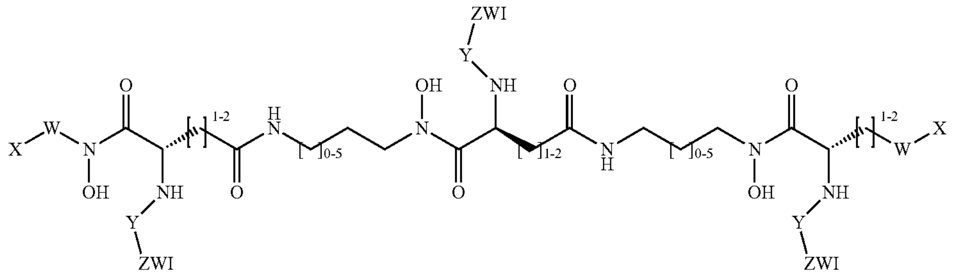
$(ZWI)_3$-DFO-$X_2$
V3
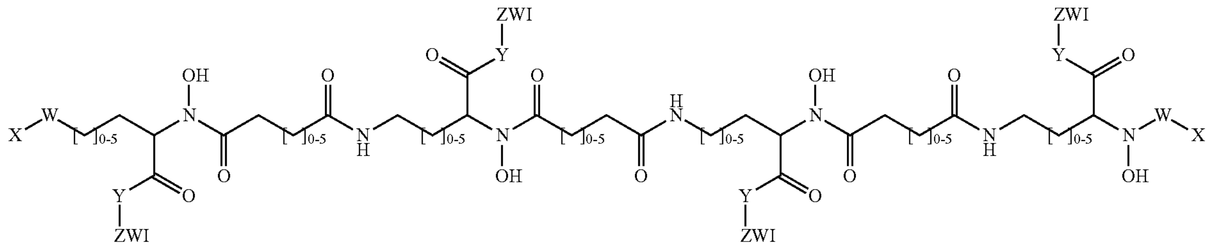
$(ZWI)_4$-DFO*-$X_2$
V3a
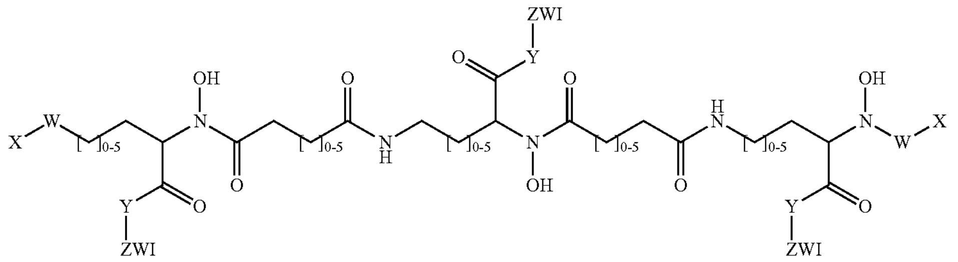
$(ZWI)_3$-DFO-$X_2$
V3b
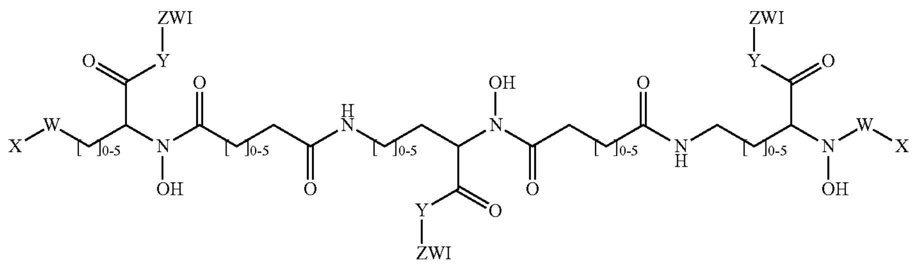
$(ZWI)_3$-DFO-$X_2$ -continued

V4

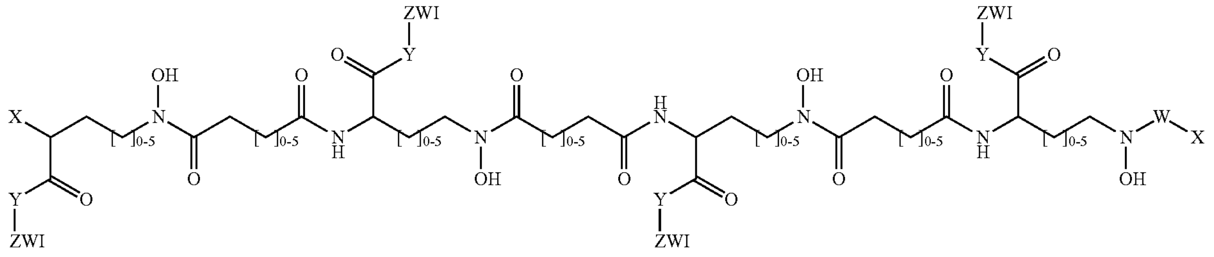

$(ZWI)_4$-DFO*-$X_2$

V4a

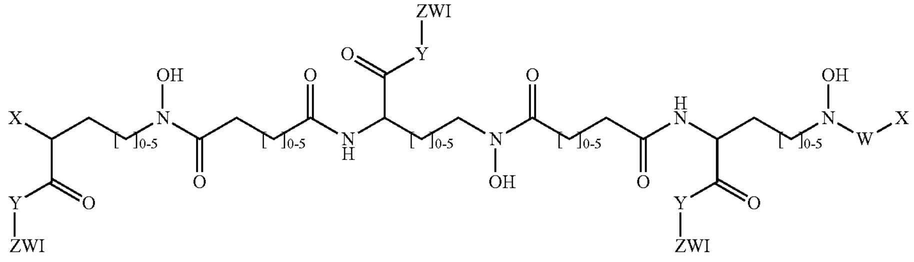

$(ZWI)_3$-DFO-$X_2$

V4b

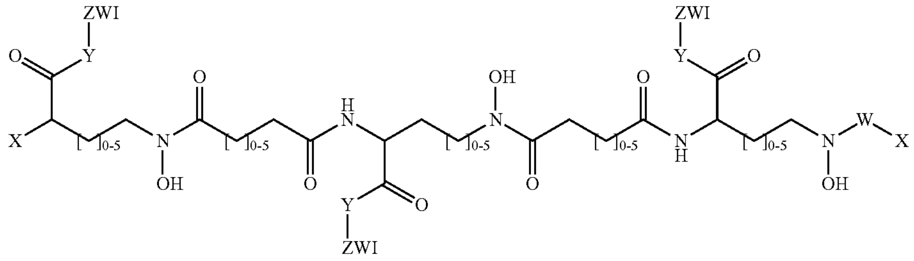

$(ZWI)_3$-DFO-$X_2$

In such embodiments, a deferoxamine-based zwitterionic metal chelator with four hydroxamate groups is derived from DFO* and one with three hydroxamate groups is derived from DFO. A deferoxamine-based zwitterionic metal chelator includes 1, 2, 3 or 4 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In still other embodiments, W-X can represent a hydrogen or an alkyl group.

In certain embodiments, the chelator comprises a reactive linking group, typically an activated derivative of a carboxylic acid, such as an NHS ester, a sulfo-NHS ester, a PFP ester, a HOBt ester, a HOAt ester, a TFP ester, an acid anhydride, an acid azide or an acid halide. Such reactive linking groups can be bound or substituted onto the chelator at any suitable structural location as would be understood by one of ordinary skill in the synthesis of such compounds.

Figure 6:
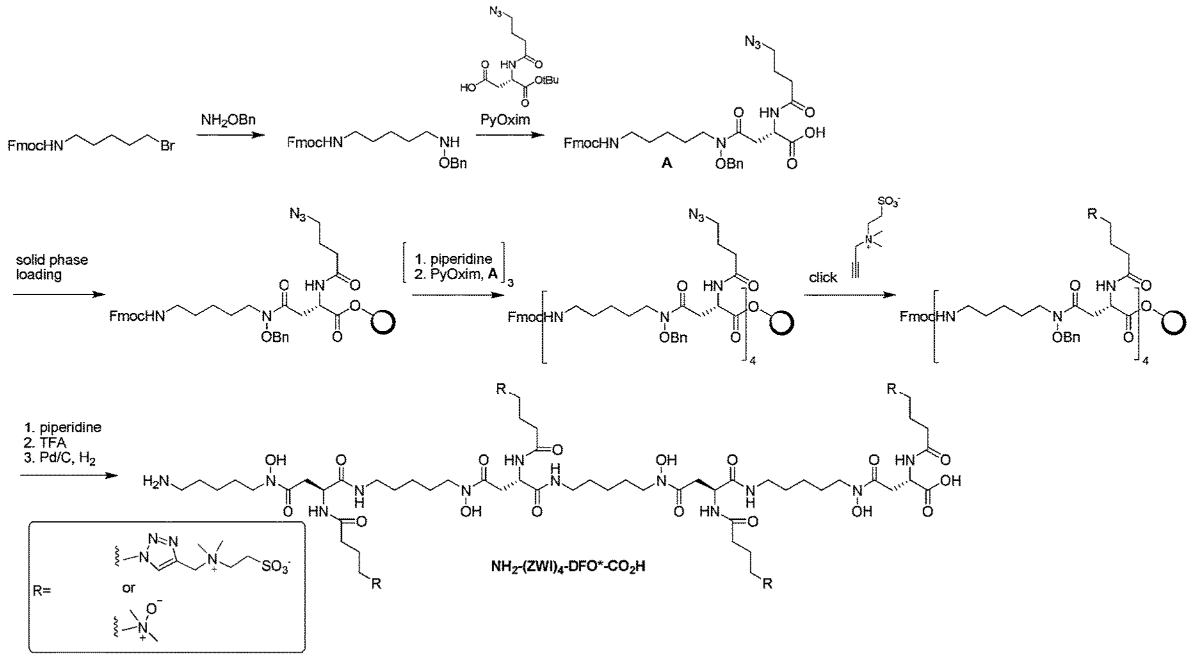
FIG. 6 is a representation of the synthesis of ZW-deferoxamine (Scheme 7)

Such deferoxamine-based zwitterionic metal chelators can be synthesized using the protocol described in Scheme 7 (FIG. 6).

In a particular embodiment, the deferoxamine-based zwitterionic metal chelators can be complexed with $Zr^{4+}$, $Fe^{3+}$, $Mn^{2+}$, $Mn^{3+}$, or similar metal cations.

In still other embodiments, the deferoxamine-based zwitterionic metal chelator can be conjugated with a targeting vector, such as cRGD, dPSMA-617, KUE, a FAP-targeting small molecule, octreotide, bombesin, octreotide, or their corresponding homo- and heterodimers, provided that the deferoxamine-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. The targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety. On the other hand, other reactive groups X can be used for conjugation of the targeting vector. For example, an amine group can react with an electrophile such as a carboxylic acid, an activated derivative thereof or an isocyanate to form an amide or a urea linkage. The amine might also be converted via other chemical transformations such as nucleophilic substitution or reductive amination to give physiologically stable linkages to the targeting vector. One or two reactive groups at any position of the deferoxamine-based zwitterionic chelator might be used for conjugation of one or more targeting vectors. Two examples of the resulting conjugates are shown in FIG. 10. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Exemplary conjugates of ZW-deferoxamine and targeting vectors (tv) include, but are not limited to:

In certain embodiments, the agent further comprises a PEG-moiety to alter the circulation time in blood. Such moiety can be bound to the conjugate at any suitable structural location as would be understood by one of ordinary skill in the synthesis of such compounds.

Imaging Agent Conjugates cRGD Conjugates

In certain embodiments, one or more of the imaging agent conjugates in the combination includes cRGD as the targeting ligand. The imaging agent conjugates in the combination include one or more of cRGD-ZW800-1, cRGD-ZW700-1 Forte, cRGD-ZW830-1, cRGD-ZW-DOTA, cRGD-ZW-PyC3A, cRGD-ZW-Macropa, cRGD-ZW-porphyrin, cRGD-ZW-NOTA, and cRGD-ZW-Deferoxamine.

In one embodiment, the cyclic-RGD peptide as the targeting ligand has the formula:

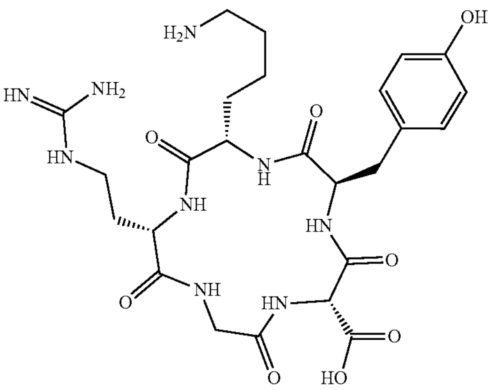 [SMILES: N=C(N)NCC[C@@H]1NC(=O)[C@H](CCCCN)NC(=O)[C@@H](Cc2ccc(O)cc2)NC(=O)[C@H](C(=O)O)NC(=O)CNC1=O]

cRGD-ZW700-1 Forte below is provided as an example for cRGD conjugates. Other cRGD conjugates, such as cRGD-ZW800-1, cRGD-ZW830-1, cRGD-ZW-DOTA, cRGD-ZW-PyC3A, cRGD-ZW-Macropa, cRGD-ZW-porphyrin, cRGD-ZW-NOTA, and cRGD-ZW-Deferoxamine can be prepared without deviating from the essence of the invention.

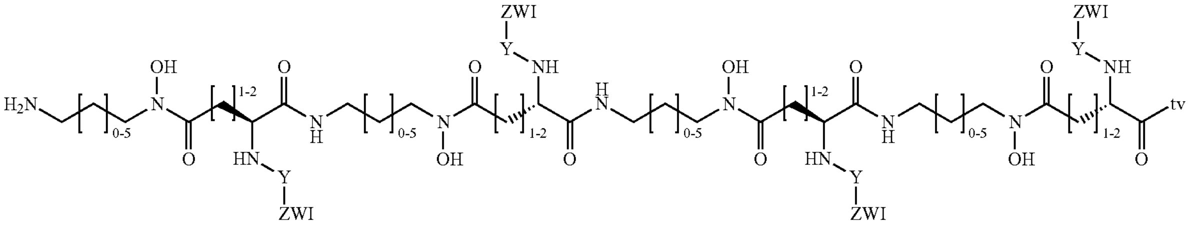

$NH_2$-$(ZWI)_4$-DFO*-tv

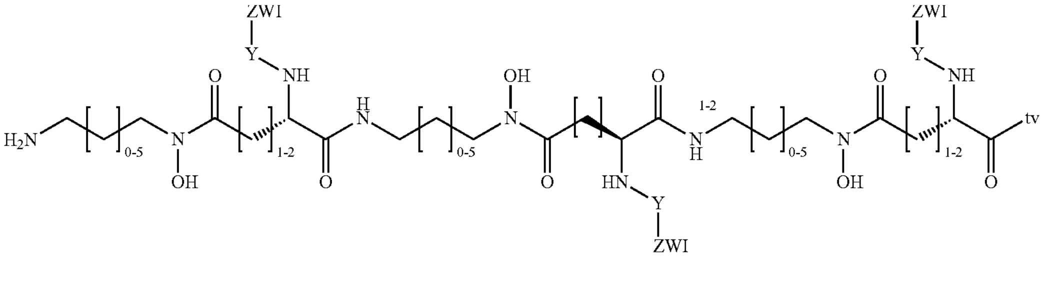

$NH_2$-$(ZWI)_3$-DFO-tv

In some embodiments, the cRGD-ZW700-1 Forte imaging agent conjugate of the invention has the following structure.

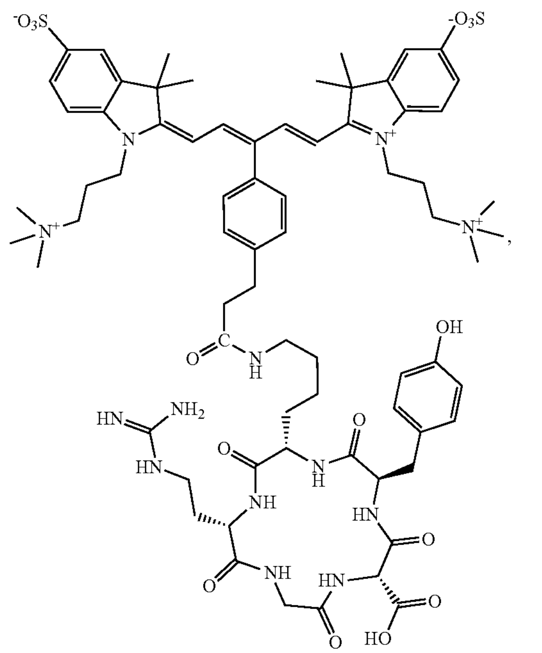

cRGD-ZW700-1c
cRGD-ZW700-1-Forte wherein L is an optional linking group.

In certain embodiments of the invention, the cRGD-ZW800-1 can have the following formula:

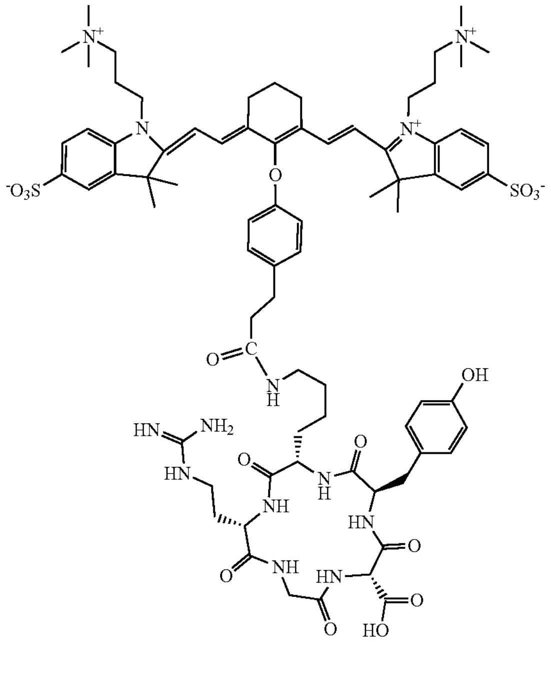

In certain embodiments of the invention, the cRGD-ZW830-1 can have the following formula:

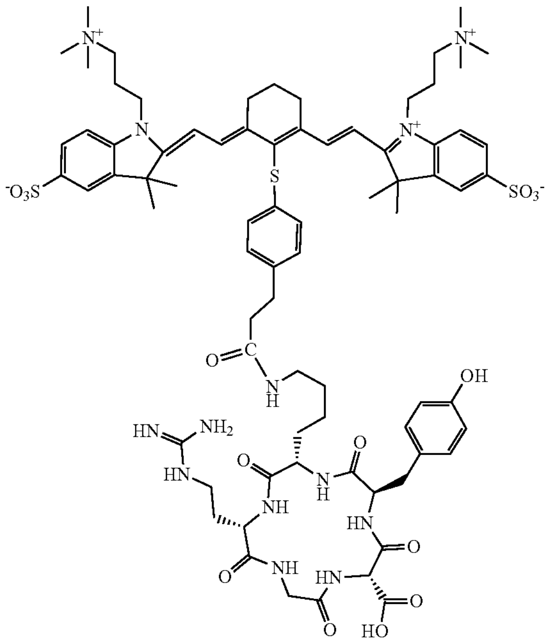

cRGD-ZW700-1 Forte Synthesis

In one aspect, the invention provides an imaging agent comprising a ZW700-1 Forte dye conjugated to a cyclic-RGD peptide targeting ligand. The conjugation can be done directly between the ZW700-1 Forte and the cRGD targeting ligand or through a linking group.

The cRDG peptide targeting ligand can be covalently attached to a reactive group of the dye compound, or through an optional linking group (L), through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. Molecular Imaging, Vol. 1(4), 354-364 (2002), each of which is incorporated herein by reference in its entirety. As used herein, "linking group" refers to any molecular entity having a molecular weight from about 50 to about 500 Da that is capable of conjugating with a targeting ligand (TL). In particular, the linking group includes at least one reactive group selected from a carboxylic acid group or anhydride or ester thereof, as well as an isothiocyanate group. In some embodiments, the linking group contains a carboxylic acid group. In some embodiments, the linking group is a PEG moiety or a straight or branched chain hydrocarbon moiety having between 2 and 12 carbon atoms. In some embodiments, the linking group includes a branching point, a reactive linking group, or other reactive group which can be used to further functionalize the imaging agent, for example, for inclusion of a radioisotope.

The present invention further provides methods of preparing a conjugate for imaging tissue or cells, wherein the conjugate includes a ZW700-1 Forte and a cRGD targeting ligand. These methods include: (a) optionally modifying the ZW700-1 Forte to include a linking group; (c) modifying the ZW700-1 Forte and optionally the linking group to include one or more ionic groups to achieve a solubility of at least about 10 μM in 10 mM HEPES solution at pH 7.4; and (d) conjugating the cRGD targeting ligand to the ZW700-1

Forte optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

ZW700-1 Forte, cRGD targeting ligands, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

The cRGD targeting ligand can be covalently attached to the reactive linking group of the dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage.

Additional details for the conjugation of dyes can be found in WO 2008/017074 and in Frangioni et al. Molecular Imaging, Vol. 1(4), 354-364 (2002), each of which is incorporated herein by reference in its entirety.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as the optional linking group between ZW700-1 Forte and the cRGD targeting ligand using methods known to one of ordinary skill in the art.

In certain embodiments, the imaging agent further comprises a radioisotope for either single-photon emission computed tomography (SPECT) or positron emission tomography (PET). Such radioisotope can be bound or further conjugated to the conjugate at any suitable structural location as would be understood by one of ordinary skill in the synthesis of such compounds.

In certain embodiments, the imaging agent further comprises a reactive linking group, such as NHS ester, sulfo-NHS ester, or a TFP ester. Such reactive linking groups can be bound or substituted onto the conjugated conjugate at any suitable structural location as would be understood by one of ordinary skill in the synthesis of such compounds.

Preparation of cRGD-ZW700-1 Forte

1. Prepare a round bottom flask equipped with magnetic stirring and charge with DMSO, 1.0 g ZW700-1 Forte (1.16 mmol), cRGD-targeting ligand (3.65 mmol) and DIEA (Sigma, 1.72 mmol). A dark solution will be observed initially.
2. After 30 minutes, precipitate the crude reaction into 300 mL of 0.1% TFA in 1:1:1 Ethanol:Ethyl Acetate:Acetone and allow this to sit for a minimum of 20 minutes.
3. Filter the solids from the precipitation in step 2, wash with ethanol (2×25 mL) and place them in a vacuum desiccator overnight to dry. A powder should be obtained.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as a linker between ZW700-1 Forte and the cRGD targeting ligand using methods known to one of ordinary skill in the art. In such instances, the PEG moiety would be bound to either the ZW700-1 Forte or the cRGD-targeting ligand prior to the preparation of the cRGD-ZW700-1 Forte moiety. Such embodiments would be referred to as PEG-cRGD-ZW700-1 Forte or cRGD-PEG-ZW700-1 Forte depending on the location of the PEG Moiety.

PSMA Conjugates

In certain embodiments, one or more of the imaging agent conjugates in the combination includes PSMA, e.g., KUE or dPSMA-617, as the targeting ligand. The imaging agent conjugates in the combination include one or more of PSMA-ZW800-1, PSMA-ZW700-1 Forte, PSMA-ZW830-1, PSMA-ZW-DOTA, PSMA-ZW-PyC3A, PSMA-ZW-Macropa, PSMA-ZW-porphyrin, PSMA-ZW-NOTA, and PSMA-ZW-Deferoxamine.

In one embodiment, PSMA includes a targeting ligand based on (((S)-5-((S)-2-((1r,4S)-4-(aminomethyl)cyclohexane-1-carboxamido)-3-(naphthalen-2-yl)propanamido)-1-carboxypentyl)carbamoyl)-L-glutamic acid, which is a derivative of PSMA-617 or Vipivotide tetraxetan. This PSMA-targeting ligand is called dPSMA-617 (for "derivative of PSMA-617) in this disclosure.

An alternative PSMA-targeting ligand is (((S)-5-amino-1-carboxypentyl)carbamoyl)-L-glutamic acid (KUE).

Figure 4:
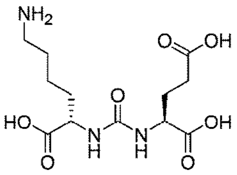
FIG. 4 is a representation of three targeting vectors of the imaging conjugates encompassed by the invention.
Figure 4:
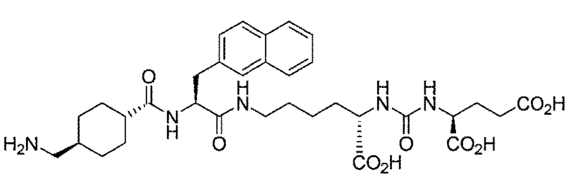
Figure 4:
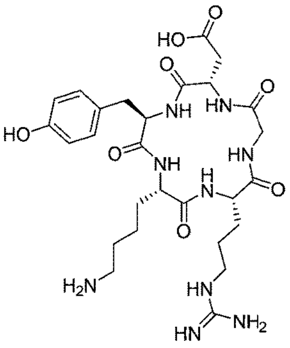

The structures of dPSMA-617 and KUE are shown in FIG. 4.

In such embodiments, a KUE or dPSMA-617-conjugated to zwitterionic metal chelator includes 1-4 zwitterionic groups as the imaging agent. In particular embodiments, the KUE or dPSMA-617-conjugated zwitterionic metal chelator includes 1-3 zwitterionic groups.

In particular embodiments, the KUE or PSMA-617-conjugated zwitterionic metal chelator has the formula:

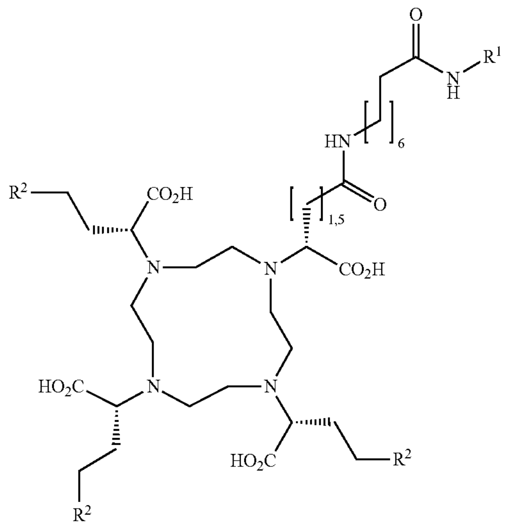

$(ZWI)_3$-DOTA-spacer-$R^1$

-continued

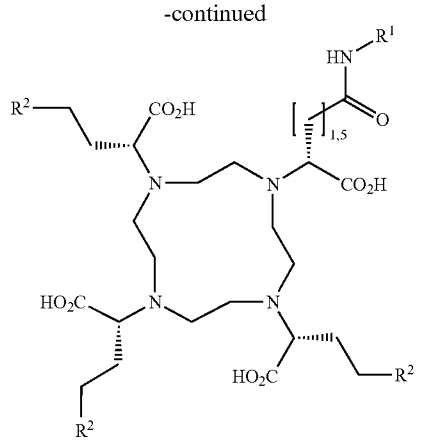

$(ZWI)_3$-DOTA-$R^1$

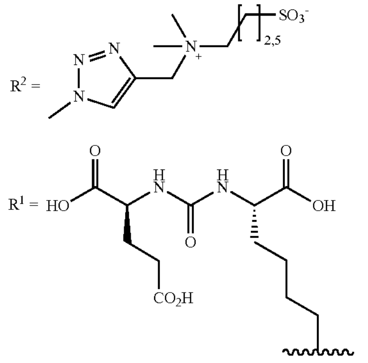

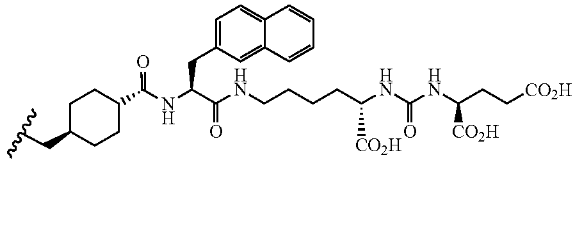

In certain embodiments of the invention, the targeting ligand according to the invention can be PSMA-617 having the following structure:

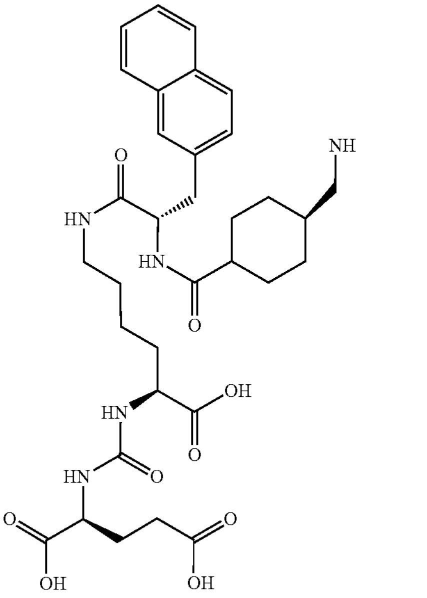

In particular embodiment, the KUE or PSMA-617-conjugated zwitterionic metal chelators can be complexed with Ga3+, Cu2+, Lu3+, Zr4+, Mn2+, Mn3+, Tb3+, Gd3+, or similar metal cations.

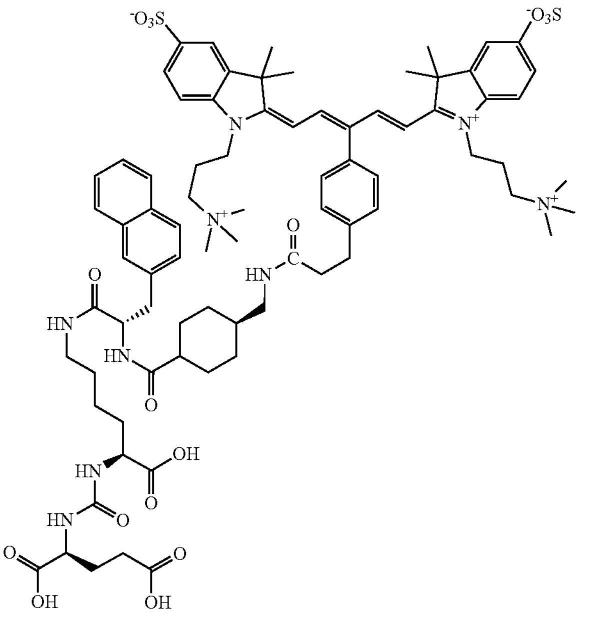

PSMA-ZW700-1 Forte wherein L is an optional linking group; or a salt, solvate, or hydrate thereof.

In certain embodiments of the invention, the PSMA-ZW800-1 can have the following formula:

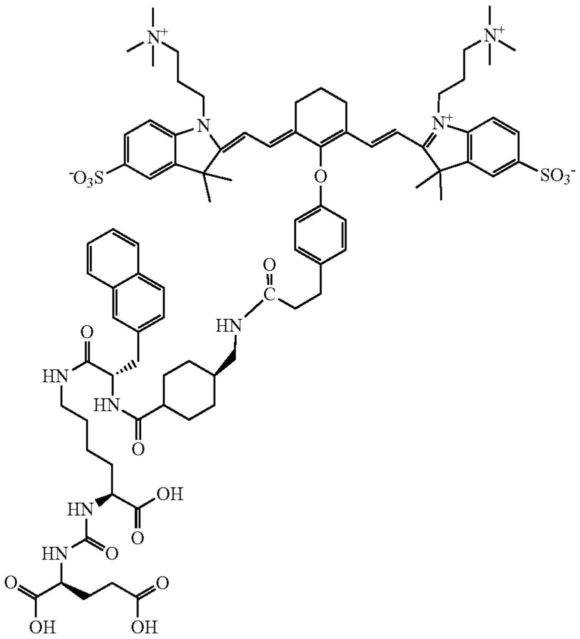

In certain embodiments of the invention, the PSMA-ZW830-1 can have the following formula:

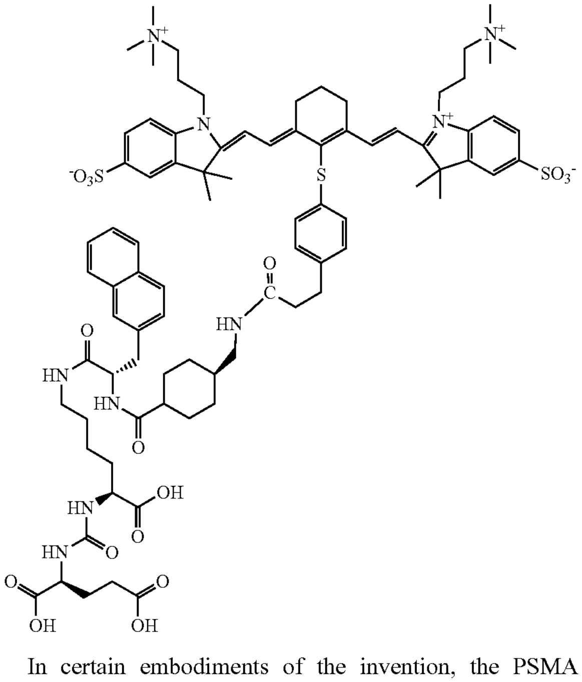

In certain embodiments of the invention, the PSMA binding vector can be KUE. In certain such embodiments, the imaging agent conjugates in the combination include one or more of KUE-ZW800-1, KUE-ZW700-1 Forte, or KUE-ZW830-1.

Provided below are examples for KUE conjugates for embodiments of the imaging agents, including KUE-ZW800-1, KUE-ZW830-1, or KUE-ZW700-1-Forte. The targeting ligand can be conjugated to the imaging dye by an optional linking group or via direct bond. As shown herein, the imaging targeting ligand is conjugated to the imaging dye via linking group (L). Nevertheless, other conjugating linkages can be used as determined by one of skill in the art. Other PSMA617 conjugates can be prepared without deviating from the essence of the invention.

In certain embodiments of the invention, the KUE-ZW-800-1 can have the following formula:

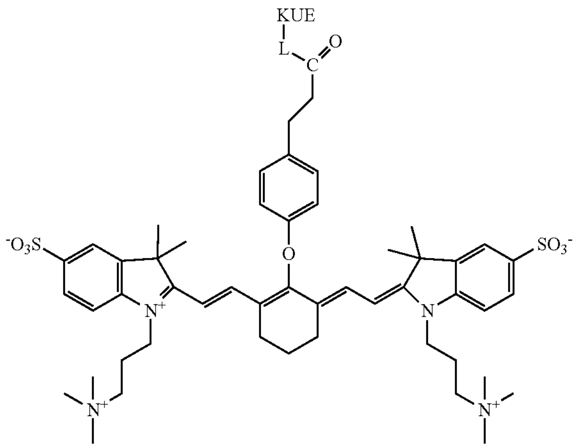

In certain embodiments of the invention, the KUE-ZW830-1 can have the following formula:

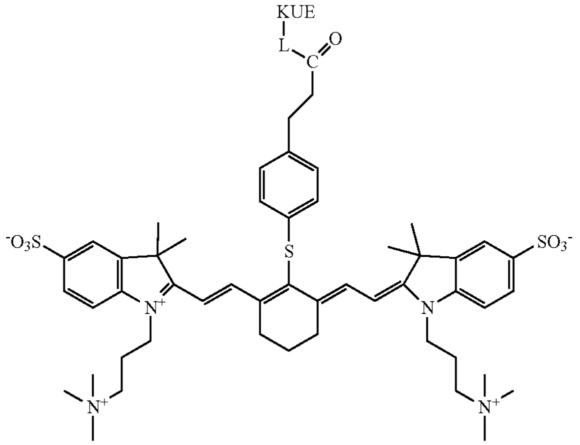

In certain embodiments of the invention, the KUE-ZW-700-Forte can have the following formula:

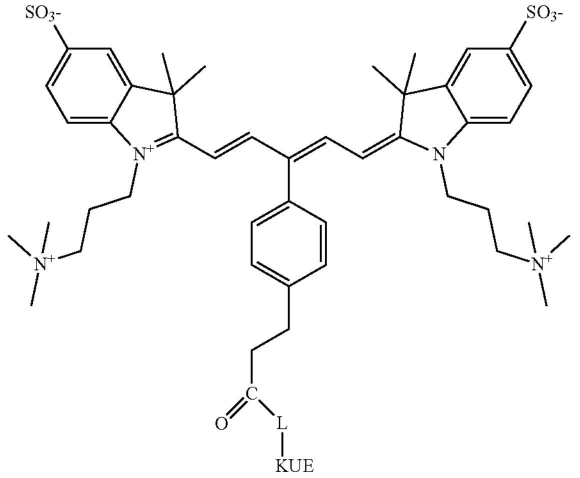

PSMA-ZW700-1 Forte is provided as an example for PSMA conjugates. Other PSMA conjugates, such as PSMA-ZW800-1, PSMA-ZW830-1, PSMA-ZW-DOTA, PSMA-ZW-PyC3A, PSMA-ZW-Macropa, PSMA-ZW-porphyrin, PSMA-ZW-NOTA, and PSMA-ZW-Deferoxamine can be prepared without deviating from the essence of the invention.

PSMA-ZW700-1 Forte Synthesis

In one aspect, the invention provides an imaging agent comprising a ZW700-1 Forte dye conjugated to a PSMA targeting ligand. The conjugation can be done directly between the ZW700-1 Forte and the PSMA targeting ligand or through a linking group. The PSMA targeting ligand can be covalently attached to a reactive group of the dye compound, or through an optional linking group (L), through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. Molecular Imaging, Vol. 1(4), 354-364 (2002), each of which is incorporated herein by reference in its entirety. As used herein, "linking group" refers to any molecular entity having a molecular weight from about 50 to about 500 Da that is capable of conjugating with a targeting ligand (TL). In particular, the linking group includes at least one reactive group selected from a carboxylic acid group or anhydride or ester thereof, as well as an isothiocyanate group. In some embodiments, the linking group contains a carboxylic acid group. In some embodiments, the linking group is a PEG moiety or a straight or branched chain hydrocarbon moiety having between 2 and 12 carbon atoms. In some embodiments, the linking group includes a branching point, a reactive linking group, or other reactive group which can be used to further functionalize the imaging agent, for example, for inclusion of a radioisotope.

The present invention further provides methods of preparing a conjugate for imaging tissue or cells, wherein the conjugate includes a ZW700-1 Forte and a PSMA targeting ligand. These methods include: (a) optionally modifying the ZW700-1 Forte to include a linking group; (c) modifying the ZW700-1 Forte and optionally the linking group to include one or more ionic groups to achieve a solubility of at least about 10 μM in 10 mM HEPES solution at pH 7.4; and (d) conjugating the PSMA targeting ligand to the ZW700-1 Forte optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

ZW700-1 Forte, PSMA targeting ligands, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

The PSMA targeting ligand can be covalently attached to the reactive linking group of the dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage.

Additional details for the conjugation of dyes can be found in WO 2008/017074 and in Frangioni et al. Molecular Imaging, Vol. 1(4), 354-364 (2002), each of which is incorporated herein by reference in its entirety.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as the optional linking group between ZW700-1 Forte and the PSMA targeting ligand using methods known to one of ordinary skill in the art.

In certain embodiments, the imaging agent further comprises a radioisotope for either single-photon emission computed tomography (SPECT) or positron emission tomography (PET). Such radioisotope can be bound or further conjugated to the conjugate at any suitable structural location as would be understood by one of ordinary skill in the synthesis of such compounds.

In certain embodiments, the imaging agent further comprises a reactive linking group, such as NHS ester, sulfo-NHS ester, or a TFP ester. Such reactive linking groups can be bound or substituted onto the conjugated conjugate at any suitable structural location as would be understood by one of ordinary skill in the synthesis of such compounds.

Preparation of PSMA-ZW700-1 Forte can be accomplished using the same method for preparing cRGD-ZW700-1 Forte without deviating from the essence of the invention.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as a linker between ZW700-1 Forte and the PSMA targeting ligand using methods known to one of ordinary skill in the art. In such instances, the PEG moiety would be bound to either the ZW700-1 Forte or the PSMA-targeting ligand prior to the preparation of the PSMA-ZW700-1 Forte moiety. Such embodiments would be referred to as PEG-PSMA-ZW700-1 Forte or PSMA-PEG-ZW700-1 Forte depending on the location of the PEG Moiety.

FAP Conjugates

In certain embodiments, one or more of the imaging agent conjugates in the combination includes FAP as the targeting ligand. The imaging agent conjugates in the combination include one or more of FAP-ZW800-1, FAP-ZW700-1 Forte, FAP-ZW830-1, FAP-ZW-DOTA, FAP-ZW-PyC3A, FAP-ZW-Macropa, FAP-ZW-porphyrin, FAP-ZW-NOTA, and FAP-ZW-Deferoxamine.

In certain embodiments, one or more of the imaging agent conjugates in the combination includes a FAP-targeting molecule (FAP-inhibitor or FAPI) as the targeting ligand.

In certain embodiments, the FAPI-targeting ligand includes $NH_2$-FAPI-74. Specific details regarding $NH_2$-FAPI-74 are described in: Linder et al., "Radioligands Targeting Fibroblast Activation Protein (FAP)," the entirety of which is incorporated herein by reference. In general, $NH_2$-FAPI-74 has the following structure: the FAPI-targeting ligand includes $NH_2$-FAPI-74

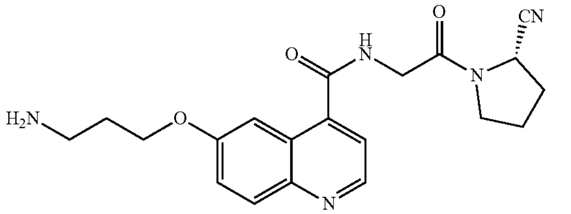

NH$_2$-FAPI-74

FAP-ZW700-1 Forte and FAP-ZW800-1 below are provided as examples for FAP conjugates. Other FAP conjugates, such as FAP-ZW830-1, FAP-ZW-DOTA, FAP-ZW-PyC3A, FAP-ZW-Macropa, FAP-ZW-porphyrin, FAP-ZW-NOTA, and FAP-ZW-Deferoxamine can be prepared without deviating from the essence of the invention.

In some embodiments, the FAP-ZW800-1 imaging agent conjugate of the invention has the following structure.

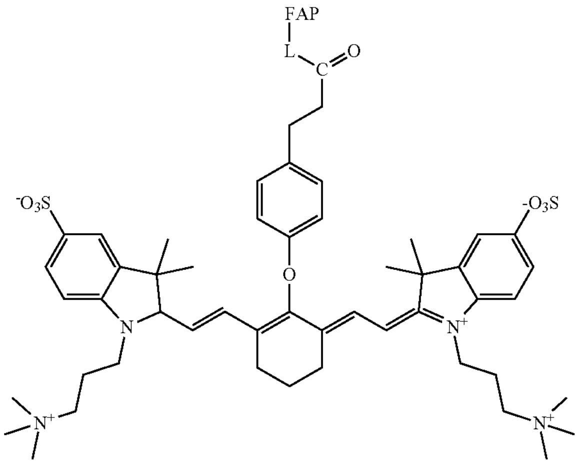

wherein L is an optional linking group; or a salt, solvate, or hydrate thereof.

In some embodiments, the FAP-ZW830-1 imaging agent conjugate of the invention has the following structure.

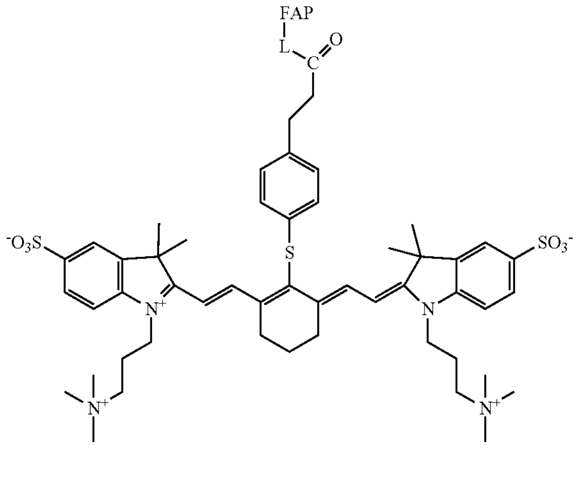

In some embodiments, the FAP-ZW700-1 Forte imaging agent conjugate of the invention has the following structure.

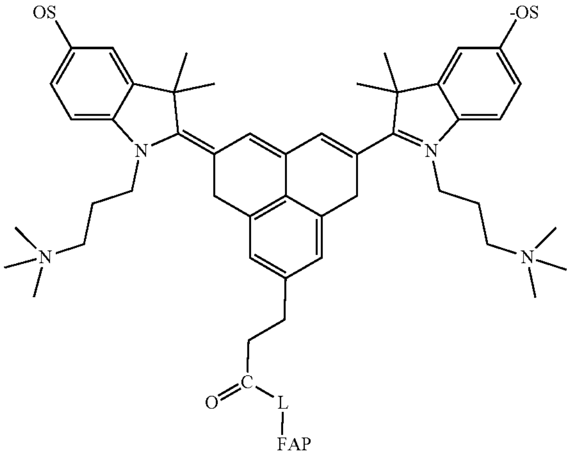

wherein L is an optional linking group; or a salt, solvate, or hydrate thereof.

FAP-ZW700-1 Forte/FAP-ZW800-1 Synthesis

In one aspect, the invention provides an imaging agent comprising a ZW700-1 Forte dye conjugated to a FAP peptide targeting ligand. The conjugation can be done directly between the ZW700-1 Forte and the FAP targeting ligand or through a linking group.

In one aspect, the invention provides an imaging agent comprising a ZW700-1 Forte dye conjugated to a FAP peptide targeting ligand. The conjugation can be done directly between the ZW800-1 and the FAP targeting ligand or through a linking group.

The FAP peptide targeting ligand can be covalently attached to a reactive group of the dye compound, or through an optional linking group (L), through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. Molecular Imaging, Vol. 1(4), 354-364 (2002), each of which is incorporated herein by reference in its entirety. As used herein, "linking group" refers to any molecular entity having a molecular weight from about 50 to about 500 Da that is capable of conjugating with a targeting ligand (TL). In particular, the linking group includes at least one reactive group selected from a carboxylic acid group or anhydride or ester thereof, as well as an isothiocyanate group. In some embodiments, the linking group contains a carboxylic acid group. In some embodiments, the linking group is a PEG moiety or a straight or branched chain hydrocarbon moiety having between 2 and 12 carbon atoms. In some embodiments, the linking group includes a branching point, a reactive linking group, or other reactive group which can be used to further functionalize the imaging agent, for example, for inclusion of a radioisotope.

The present invention further provides methods of preparing a conjugate for imaging tissue or cells, wherein the conjugate includes a ZW700-1 Forte/ZW800-1 and a FAP targeting ligand. These methods include: (a) optionally modifying the ZW700-1 Forte/ZW800-1 to include a linking group; (c) modifying the ZW700-1 Forte/ZW-800-1 and optionally the linking group to include one or more ionic groups to achieve a solubility of at least about 10 μM in 10 mM HEPES solution at pH 7.4; and (d) conjugating the FAP targeting ligand to the ZW700-1 Forte/ZW800-1 optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

ZW700-1 Forte/ZW800-1, FAP targeting ligands, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

The FAP targeting ligand can be covalently attached to the reactive linking group of the dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage.

Additional details for the conjugation of dyes can be found in WO 2008/017074 and in Frangioni et al. Molecular Imaging, Vol. 1(4), 354-364 (2002), each of which is incorporated herein by reference in its entirety.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as the optional linking group between ZW700-1 Forte/ZW800-1 and the FAP targeting ligand using methods known to one of ordinary skill in the art.

In certain embodiments, the imaging agent further comprises a radioisotope for either single-photon emission computed tomography (SPECT) or positron emission tomography (PET). Such radioisotope can be bound or further conjugated to the conjugate at any suitable structural location as would be understood by one of ordinary skill in the synthesis of such compounds.

In certain embodiments, the imaging agent further comprises a reactive linking group, such as NHS ester, sulfo-NHS ester, or a TFP ester. Such reactive linking groups can be bound or substituted onto the conjugated conjugate at any suitable structural location as would be understood by one of ordinary skill in the synthesis of such compounds.

Preparation of FAP-ZW700-1 Forte can be accomplished using the same method for preparing FAP-ZW700-1 Forte without deviating from the essence of the invention.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as a linker between ZW700-1 Forte/ZW800-1 and the FAP targeting ligand using methods known to one of ordinary skill in the art. In such instances, the PEG moiety would be bound to either the ZW700-1 Forte/ZW800-1 or the FAP-targeting ligand prior to the preparation of the FAP-ZW700-1 Forte/ZW800-1 moiety. Such embodiments would be referred to as PEG-FAP-ZW700-1 Forte/ZW800-1 or FAP-PEG-ZW700-1 Forte/ZW800-1 depending on the location of the PEG Moiety.

Bombesin Receptor Conjugates

In certain embodiments, one or more of the imaging agent conjugates in the combination includes bombesin as the targeting ligand. The imaging agent conjugates in the combination include one or more of Bombesin-ZW800-1, Bombesin-ZW700-1 Forte, Bombesin-ZW830-1, Bombesin-ZW-DOTA, Bombesin-ZW-PyC3A, Bombesin-ZW-Macropa, Bombesin-ZW-porphyrin, Bombesin-ZW-NOTA, and Bombesin-ZW-Deferoxamine.

In general, the structure of bombesin (SEQ ID No: 6) is:

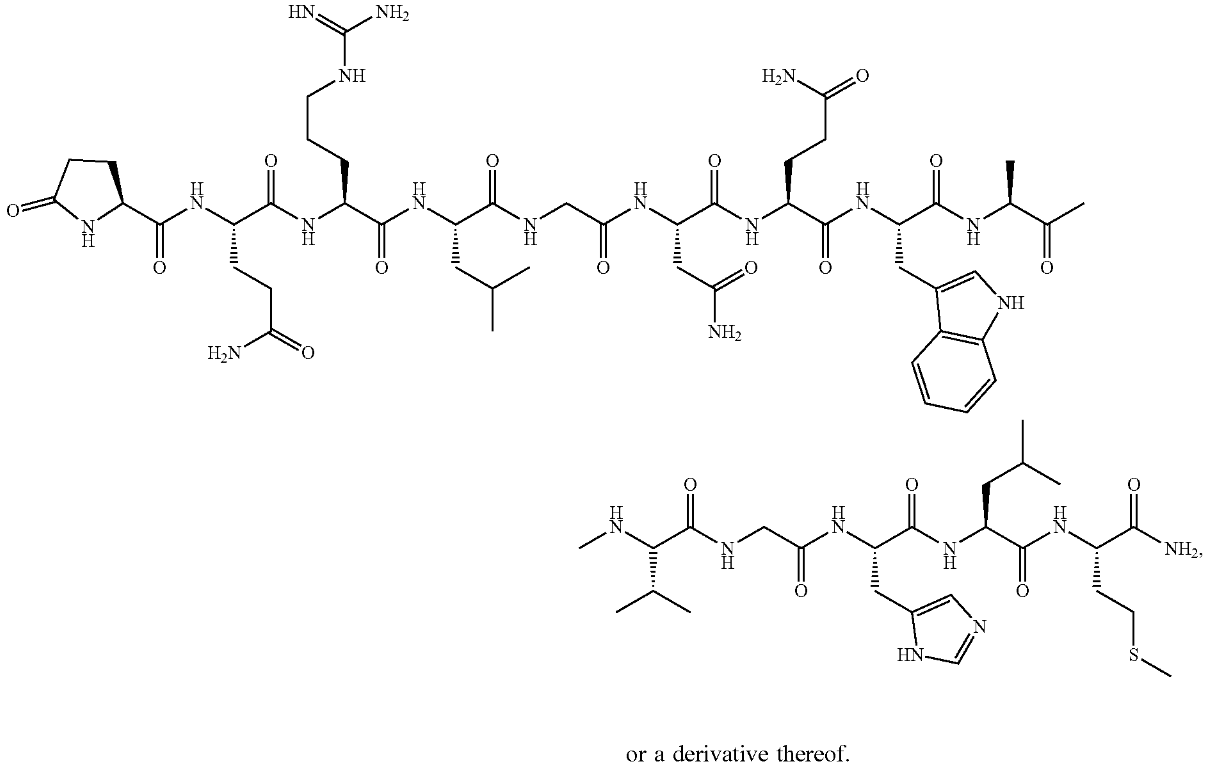

or a derivative thereof.

Bombesin-ZW700-1 Forte below is provided as an example for bombesin conjugates. Other bombesin conjugates, such as Bombesin-ZW800-1, Bombesin-ZW700-1 Forte, Bombesin-ZW830-1, Bombesin-ZW-DOTA, Bombesin-ZW-PyC3A, Bombesin-ZW-Macropa, Bombesin-ZW-porphyrin, Bombesin-ZW-NOTA, and Bombesin-ZW-Deferoxamine can be prepared without deviating from the essence of the invention.

In certain embodiments of the invention, the BOMBESIN-ZW-800-1 can have the following formula:

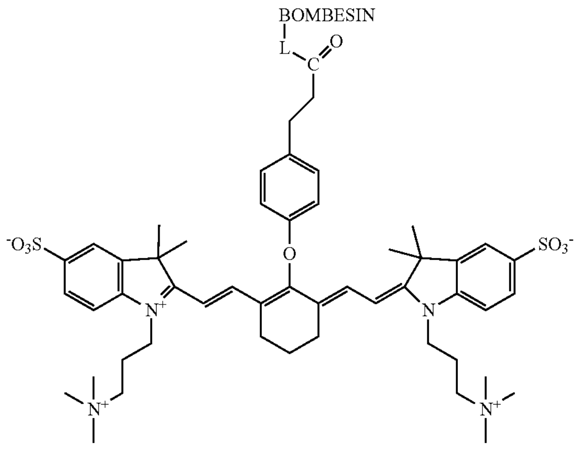

In certain embodiments of the invention, the BOMBESIN-ZW830-1 can have the following formula:

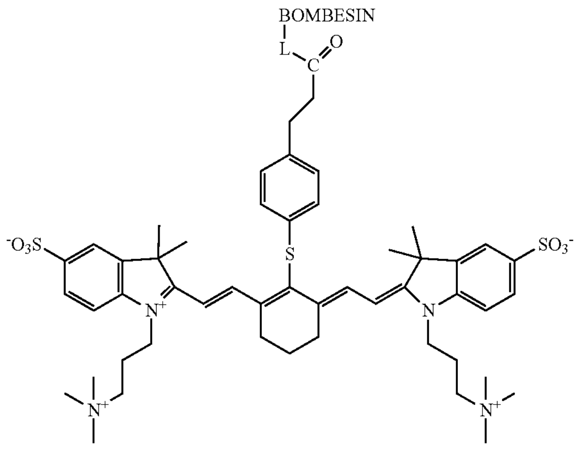

In certain embodiments of the invention, the BOMBESIN-ZW-700-Forte can have the following formula:

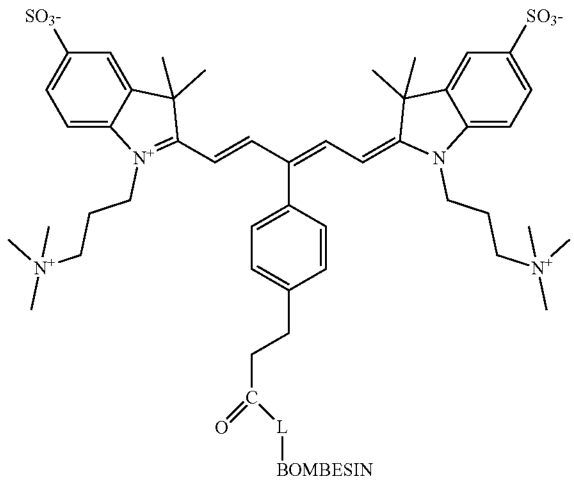

Bombesin-ZW700-1 Forte Synthesis

In one aspect, the invention provides an imaging agent comprising a ZW700-1 Forte dye conjugated to a bombesin receptor as the targeting ligand. The conjugation can be done directly between the ZW700-1 Forte and the bombesin receptor or through a linking group.

The bombesin receptor targeting ligand can be covalently attached to a reactive group of the dye compound, or through an optional linking group (L), through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. Molecular Imaging, Vol. 1(4), 354-364 (2002), each of which is incorporated herein by reference in its entirety. As used herein, "linking group" refers to any molecular entity having a molecular weight from about 50 to about 500 Da that is capable of conjugating with a targeting ligand (TL). In particular, the linking group includes at least one reactive group selected from a carboxylic acid group or anhydride or ester thereof, as well as an isothiocyanate group. In some embodiments, the linking group contains a carboxylic acid group. In some embodiments, the linking group is a PEG moiety or a straight or branched chain hydrocarbon moiety having between 2 and 12 carbon atoms. In some embodiments, the linking group includes a branching point, a reactive linking group, or other reactive group which can be used to further functionalize the imaging agent, for example, for inclusion of a radioisotope.

The present invention further provides methods of preparing a conjugate for imaging tissue or cells, wherein the conjugate includes a ZW700-1 Forte and a bombesin targeting ligand. These methods include: (a) optionally modifying the ZW700-1 Forte to include a linking group; (c) modifying the ZW700-1 Forte and optionally the linking group to include one or more ionic groups to achieve a solubility of at least about 10 μM in 10 mM HEPES solution at pH 7.4; and (d) conjugating the bombesin targeting ligand to the ZW700-1 Forte optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

ZW700-1 Forte, bombesin targeting ligands, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

The bombesin targeting ligand can be covalently attached to the reactive linking group of the dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage.

Additional details for the conjugation of dyes can be found in WO 2008/017074 and in Frangioni et al. Molecular Imaging, Vol. 1(4), 354-364 (2002), each of which is incorporated herein by reference in its entirety.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as the optional linking group between ZW700-1 Forte and the bombesin targeting ligand using methods known to one of ordinary skill in the art.

In certain embodiments, the imaging agent further comprises a radioisotope for either single-photon emission computed tomography (SPECT) or positron emission tomography (PET). Such radioisotope can be bound or further conjugated to the conjugate at any suitable structural location as would be understood by one of ordinary skill in the synthesis of such compounds.

In certain embodiments, the imaging agent further comprises a reactive linking group, such as NHS ester, sulfo-NHS ester, or a TFP ester. Such reactive linking groups can be bound or substituted onto the conjugated conjugate at any suitable structural location as would be understood by one of ordinary skill in the synthesis of such compounds.

Preparation of bombesin-ZW700-1 Forte can be accomplished using the same method for preparing bombesin-ZW700-1 Forte without deviating from the essence of the invention.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as a linker between ZW700-1 Forte and the bombesin targeting ligand using methods known to one of ordinary skill in the art. In such instances, the PEG moiety would be bound to either the ZW700-1 Forte or the bombesin-targeting ligand prior to the preparation of the bombesin-ZW700-1 Forte moiety. Such embodiments would be referred to as PEG-bombesin-ZW700-1 Forte or bombesin-PEG-ZW700-1 Forte depending on the location of the PEG Moiety.

Octreotide Conjugates

In certain embodiments, one or more of the imaging agent conjugates in the combination includes octreotide as the targeting ligand. The imaging agent conjugates in the combination include one or more of octreotide-ZW800-1, octreotide-ZW700-1 Forte, octreotide-ZW830-1, octreotide-ZW-DOTA, octreotide-ZW-PyC3A, octreotide-ZW-Macropa, octreotide-ZW-porphyrin, octreotide-ZW-NOTA, and octreotide-ZW-Deferoxamine.

In general, the structure of octreotide (SEQ ID No: 5) is:

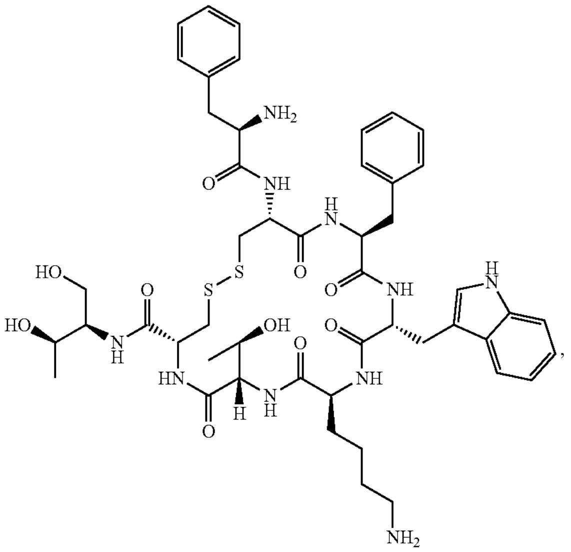 [SMILES: C[C@@H](O)[C@@H]1NC(=O)[C@H](CCCCN)NC(=O)[C@@H](Cc2c[nH]c3ccccc23)NC(=O)[C@H](Cc2ccccc2)NC(=O)[C@@H](NC(=O)[C@H](N)Cc2ccccc2)CSSC[C@@H](C(=O)N[C@H](CO)[C@@H](C)O)NC1=O]

or a derivative thereof.

Octreotide-ZW700-1 Forte below is provided as an example for octreotide conjugates. Other octreotide conjugates, such as octreotide-ZW800-1, octreotide-ZW700-1 Forte, octreotide-ZW830-1, octreotide-ZW-DOTA, octreotide-ZW-PyC3A, octreotide-ZW-Macropa, octreotide-ZW-porphyrin, octreotide-ZW-NOTA, and octreotide-ZW-Deferoxamine can be prepared without deviating from the essence of the invention.

In certain embodiments of the invention, the octreotide-ZW-800-1 can have the following formula:

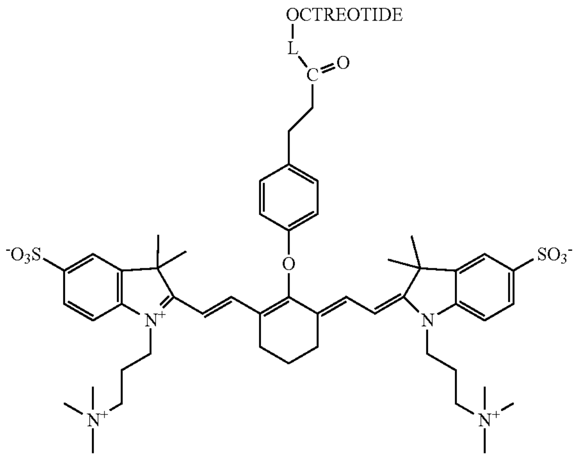

In certain embodiments of the invention, the OCTREOTIDE-ZW-830-1 can have the following formula:

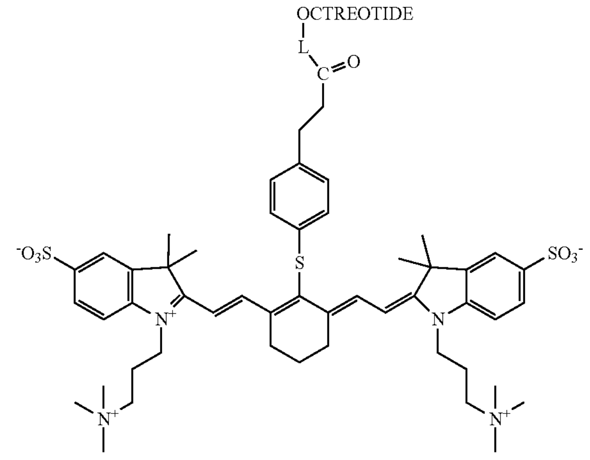

In certain embodiments of the invention, the OCTREOTIDE-ZW700-1-Forte can have the following formula:

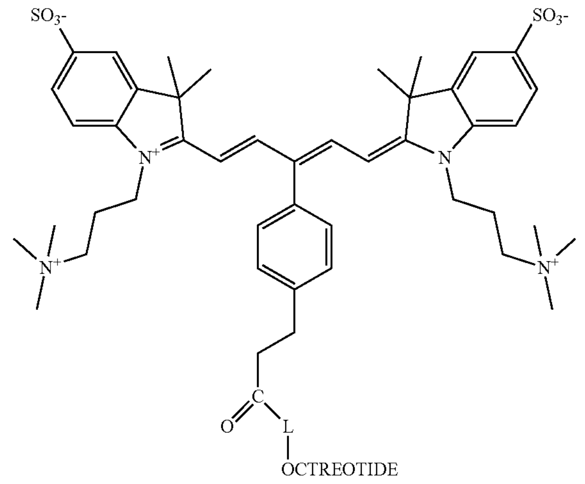

Octreotide-ZW700-1 Forte Synthesis

In one aspect, the invention provides an imaging agent comprising a ZW700-1 Forte dye conjugated to a octreotide as the targeting ligand. The conjugation can be done directly between the ZW700-1 Forte and the octreotide or through a linking group.

The octreotide targeting ligand can be covalently attached to a reactive group of the dye compound, or through an optional linking group (L), through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. Molecular Imaging, Vol. 1(4), 354-364 (2002), each of which is incorporated herein by reference in its entirety. As used herein, "linking group" refers to any molecular entity having a molecular weight from about 50 to about 500 Da that is capable of conjugating with a targeting ligand (TL). In particular, the linking group includes at least one reactive group selected from a carboxylic acid group or anhydride or ester thereof, as well as an isothiocyanate group. In some embodiments, the linking group contains a carboxylic acid group. In some embodiments, the linking group is a PEG moiety or a straight or branched chain hydrocarbon moiety having between 2 and 12 carbon atoms. In some embodiments, the linking group includes a branching point, a reactive linking group, or other reactive group which can be used to further functionalize the imaging agent, for example, for inclusion of a radioisotope.

The present invention further provides methods of preparing a conjugate for imaging tissue or cells, wherein the conjugate includes a ZW700-1 Forte and a octreotide targeting ligand. These methods include: (a) optionally modifying the ZW700-1 Forte to include a linking group; (c) modifying the ZW700-1 Forte and optionally the linking group to include one or more ionic groups to achieve a solubility of at least about 10 μM in 10 mM HEPES solution at pH 7.4; and (d) conjugating the octreotide targeting ligand to the ZW700-1 Forte optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

ZW700-1 Forte, octreotide targeting ligands, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

The octreotide targeting ligand can be covalently attached to the reactive linking group of the dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage.

Additional details for the conjugation of dyes can be found in WO 2008/017074 and in Frangioni et al. Molecular Imaging, Vol. 1(4), 354-364 (2002), each of which is incorporated herein by reference in its entirety.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as the optional linking group between ZW700-1 Forte and the bombesin targeting ligand using methods known to one of ordinary skill in the art.

In certain embodiments, the imaging agent further comprises a radioisotope for either single-photon emission computed tomography (SPECT) or positron emission tomography (PET). Such radioisotope can be bound or further conjugated to the conjugate at any suitable structural location as would be understood by one of ordinary skill in the synthesis of such compounds.

In certain embodiments, the imaging agent further comprises a reactive linking group, such as NHS ester, sulfo-NHS ester, or a TFP ester. Such reactive linking groups can be bound or substituted onto the conjugated conjugate at any suitable structural location as would be understood by one of ordinary skill in the synthesis of such compounds.

Preparation of octreotide-ZW700-1 Forte can be accomplished using the same method for preparing octreotide-ZW700-1 Forte without deviating from the essence of the invention.

In certain embodiments, the imaging agent further comprises a PEG-moiety. Such moiety can be bound to the conjugate at any suitable structural location as would be understood by one of ordinary skill in the synthesis of such compounds. In addition, in certain embodiments, the PEG-moiety can be included as a linker between ZW700-1 Forte and the octreotide targeting ligand using methods known to one of ordinary skill in the art. In such instances, the PEG moiety would be bound to either the ZW700-1 Forte or the octreotide-targeting ligand prior to the preparation of the octreotide-ZW700-1 Forte moiety. Such embodiments would be referred to as PEG-octreotide-ZW700-1 Forte or octreotide-PEG-ZW700-1 Forte depending on the location of the PEG Moiety.

Other Targeting Ligand for Conjugated to the Imaging Agents

In certain embodiment, the synthetic protocol described in Scheme 2 can be used to conjugate the imaging agents of ZW700-1 Forte, ZW800-1, ZW830-1, ZW-DOTA, ZW-NOTA, ZW-porphyrin, ZW-deferoxamine and ZW-Py3CA to the targeting ligand including cRGD, a FAP-targeting molecule, octreotide, or dimers including a combination of cRGD, dPSMA-617, a FAP-targeting molecule, octreotide, octreotide, and bombesin.

In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

Depending on the reactive group of the imaging agents, other common chemical methods may be used to conjugate the targeting ligand, such as azide-alkyne-cycloadditions, nucleophilic displacements, Diels-Alder-reactions, urea and urethane formations, thiol-ene conjugations or similar conversions. For some of these conversions derivatives of KUE or dPSMA-617 with other reactive functional groups can be used. For example a conjugation via a copper-catalyzed azide-alkyne-cycloaddition could require either an alkyne or an azide group as the reactive group at the zwitterionic chelator and a matching alkyne or azide group as the reactive group at the targeting vector.

In certain embodiments, the targeting ligand can further include a molecular scaffold moiety to which the binding moiety and other groups can attach. For example, the molecule scaffold can bear one or more of the following: (1) a moiety designed to react with the reactive linking group of the dye to form a covalent bond, (2) a charge balancing moiety, such as any of the ionic groups described herein, and (3) a moiety that binds to the biological target. An example of a molecular scaffold is an adamantane derivative, such as described in U.S. Pat. App. Pub. No. 2006/0063834, which is incorporated herein by reference in its entirety, and illustrates the preparation of a targeting ligand that incorporates an adamantane scaffold. Specifically, the adamantane core holds (1) an amino group capable of reacting with the dye compounds, (2) a charge-balancing moiety that will neutralize a negative charge on the dye molecule, and (3) two moieties that bind to the biological target PSMA. For a description of moieties that bind to PSMA, see, Humblet, V. et al. Mol. Imaging, 2005, 4: 448-62; Misra P. et al. J. Nucl. Med. 2007, 48: 1379-89; Chen, Y, et al. J. Med. Chem, 2008, 51: 7933-43; Chandran, S. S., et al. Cancer Biol. Ther., 2008, 7:974-82; Banerjee, S. R., J. Med. Chem. 2008, 51: 4504-17; Mease, R. C., et al. Clin. Cancer Res., 2008, 14:3036-43; Foss, C. A. et al. Clin. Cancer. Res., 2005, 11:4022-8, each of which is incorporated herein by reference in its entirety.

Imaging Methods

In one aspect, the invention provides for methods of biomedical imaging of tissues or cells in a biological sample. In particular embodiment, the invention encompasses a method for detecting or imaging one or more cancer cells in a biological sample.

In some embodiments, the method is suitable for imaging of abnormal, but not malignant, tissue, such as defects of the musculoskeletal system using FAP as a targeting ligand, vascular system using cRGD as a targeting ligand, melanoma using LyP-1 peptide as a targeting ligand, breast cancer using K237 peptide and/or mUNO as a targeting ligand, Lung tumor, breast tumor, colon tumor using IL4RPep-1 as a targeting ligand.

In some embodiments, the method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In some embodiments, the cancer cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In particular embodiments, the cancer cells are prostate cancer cells.

In some embodiments, the biological sample is part or all of a subject. In some embodiments, the biological sample is obtained from a subject.

In particular embodiments, the method includes the steps of (a) contacting the biological sample with a combination of the imaging agent conjugates described above, wherein each of the imaging agent conjugates in the combination comprises a targeting ligand linked to an imaging agent. The imaging agent is capable of being detected by one or more conventional scanning methods.

In some embodiments, the compound is administered by parenteral, intranasal, sublingual, rectal, or transdermal delivery. In some such embodiments, the compound is administered intravenously. In some embodiments, the compound is administered intratumorally.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In particular embodiments, the subject is a human.

The methods of imaging tissue or cells include the following basic steps:

(a) contacting the tissue or cells with a combination of imaging agent conjugates; and (b) imaging the tissue or cells using positron emission tomography (PET), single-photon emission computerized tomography (SPECT), or magnetic resonance imaging (MRI).

The imaging agent conjugate described herein is a substance to that can be used to image tissues or cells, such as those of a living organism, for purposes of diagnosis, therapy, image-guided surgery, and the like. In some embodiments, the organism is a mammal, such as a human.

The imaging agent conjugates described herein generally has improved "signal-to-background ratio" (SBR) compared to presently known imaging agents. The improvement in SBR is believed to be a result of improved in vivo properties due to "charge-balancing." SBR is a measure of the intensity of the signal obtained from a target (peak signal) over the measure of the intensity of the signal obtained nearby the target (background signal), the target being the tissues or cells targeted by the imaging agent. SBR measurements can be readily obtained through routine measurement procedures. Higher SBR values are more desirable, resulting in greater resolution of the imaged tissues. In some embodiments, the imaging agents achieve an SBR of at least about 1.1 (i.e., peak signal is at least 10% over background). In further embodiments, the imaging agents achieve an SBR of at least about 1.2, at least about 1.3, at least about 1.4, at least about 1.5, at least about 1.6, at least about 1.7, at least about 1.8, at least about 1.9, or at least about 2.0. In yet further embodiments, the imaging agents achieve an SBR of about 1.1 to about 50, about 1.5 to about 30, about 2.0 to about 20, about 2.0 to about 5.0, or about 5.0 to about 10.

In another aspect, the disclosure encompasses a method of measuring and/or monitoring the effectiveness of various biological functions of a subject. In particular embodiments, the method provides for measuring the effectiveness of hepatic function, renal function, or blood pooling in a subject. In such embodiments, the zwitterionic metal chelators may be used with or without the addition of a targeting ligand. The method includes the step of administering to a subject in need of measurement of a biological function with a quantifiable amount of one or more of the zwitterionic metal chelators described above; imaging the subject using positron emission tomography (PET), single-photon emission computerized tomography (SPECT), or magnetic resonance imaging (MRI); and determining the amount of the zwitterionic metal chelator present in the biological function being observed.

Treatment, Diagnosis, and Monitoring Methods

Cancerous Conditions

In another aspect, the disclosure encompasses a method for inhibiting the proliferation or growth of malignant or non-malignant cells. The method includes the step of contacting one or more cells with an effective amount of a combination of imaging agent conjugates described above.

In some embodiments, the method is performed in vivo, ex vivo, or in vitro.

In some embodiments, the malignant cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In another aspect, the disclosure encompasses a method of diagnosing cancer in a subject. The method includes one or more of the imaging/detection steps outlined above. In the method, the biological sample is obtained from, part of, or all of a subject. If cancer cells are detected or imaged in the method steps, the subject is diagnosed with cancer. In certain embodiments, the method of diagnosing cancer in a subject is followed by a step of treating the subject diagnosed with cancer with a cancer therapy. In some embodiments, the cancer therapy is, surgery, chemotherapy or radiotherapy.

In some embodiments, the cancer that is diagnosed is an adult solid tumor or a pediatric solid tumor. Non-limiting examples of such cancer include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

In still another aspect, the disclosure encompasses a method of monitoring the efficacy of a cancer therapy in a human subject. The method includes performing one or more of the imaging/detection steps outlined above at two or more different times on the biological sample, wherein the biological sample is obtained from, part of, or all of a subject. The change in strength of the signals characteristic of the metal isotope between the two or more different times is correlated with the efficacy of the cancer therapy.

In another aspect, the disclosure encompasses a method of treatment of abnormal, but not malignant, tissue, such as defects of the musculoskeletal system using FAP as a targeting ligand, vascular system using cRGD as a targeting ligand, melanoma using LyP-1 peptide as a targeting ligand, breast cancer using K237 peptide and/or mUNO as a targeting ligand, Lung tumor, breast tumor, colon tumor using IL4RPep-1 as a targeting ligand.

The method includes the step of contacting one or more abnormal cells with an effective amount of a combination of the conjugates described above, wherein the metal atom is a radioactive metal isotope known to emit ionizing radiation in a form that would result in a therapeutic effect on the cells that take up the analogs.

In another aspect, the disclosure encompasses a method of treating a cancer by administering an effective amount of a therapeutic agent comprising a combination of the conjugates and a pharmaceutically acceptable carrier or excipient. The method comprises a step to diagnose the cancer and a step of administering the therapeutic agent to a subject determined to be in need thereof;

wherein the step to diagnose the cancer comprises:

contacting cells, tissues or organs of a subject with a combination of the imaging agent conjugates, imaging the cells, tissues, or organs of the subject using positron emission tomography (PET), single-photon emission computerized tomography (SPECT), or magnetic resonance tomography (MRT), and diagnosing the cancer in the cells tissues, or organs of the subject based on imaging data collected;

and wherein the metal atom complexed to the imaging agent dyes of the conjugates is:

a radioactive metal isotope known to emit ionizing radiation that results in the death of cells that take up the analogs;

or a non-radioactive metal that is capable of releasing cytotoxic radiation upon irradiation with alpha emission, beta emission, neutron capture, or a combination thereof.

In still another aspect, the disclosure encompasses a method of treating a rare or childhood cancer by administering an effective amount of a therapeutic agent comprising a combination of conjugates described above and a pharmaceutically acceptable carrier or excipient. In such aspects, the therapeutic agent may further comprise one or more targeting ligands selected from the group consisting of cRGD, PSMA, FAP, bombesin, octreotide, octreotide or a dimer formed from their combination.

In particular embodiments, the rare or childhood cancer is: Acinic cell carcinoma, ACTH-secreting tumor, Actinic keratosis, Adamantinoma, Adenoid cystic carcinoma, Alveolar soft part sarcoma, Ampullary cancer, Angiosarcoma, Appendix (appendiceal) neuroendocrine (carcinoid) tumor, Askin tumor—a type of Ewing tumor (Ewing sarcoma), Bartholin gland cancer, Basaloid squamous cell carcinoma of the anus, Bowen disease, Bronchioloalveolar carcinoma, Carcinoid tumor, Carcinoma of the ampulla of Vater, Cardiac angiosarcoma, Castleman disease, Cholangiocarcinoma, Choriocarcinoma, Choroid plexus tumor, Chondrosarcoma, Chordoma, Chromophobe renal cell carcinoma, Clear cell sarcoma, Craniopharyngioma, Dermatofibrosarcoma protuberans, Desmoid tumor, Desmoplastic small round cell tumor, Dysgerminoma, Embryonal carcinoma, Endodermal sinus tumor, Endometrial stromal sarcoma, Ependymoma, Epithelial appendix (appendiceal) cancer, Epithelial-myoepithelial carcinoma, Epithelioid hemangioendothelioma (EHE), Epithelioid sarcoma, Essential thrombocythemia, Esthesioneuroblastoma (olfactory neuroblastoma), Extra-cranial malignant rhabdoid tumor (MRT), Extranodal NK/T-cell lymphoma—nasal type, Fallopian tube cancer, Fibrolamellar carcinoma, Fibromatosis, Fibromyxoid sarcoma (Evans' tumor), Fibrosarcoma Folliculotropic mycosis fungoides, Ganglioglioma, Ganglioneuroblastoma, Gastric Adenocarcinoma and Proximal Polyposis of the Stomach (GAPPS), Gastrinoma, Gastroesophageal junction (GEJ) cancer, Gestational trophoblastic disease (GTD) (hydatidiform mole; gestational trophoblastic neoplasia), Germ cell tumor, Giant cell tumor of bone, Glucagonoma, Granulomatous slack skin, Heart cancer (cardiac angiosarcoma), Hemangioendothelioma, Hemangiosarcoma, Hepatobiliary cancer, Hepatoblastoma, Hepatocellular carcinoma, Hepatoma, Hereditary diffuse gastric cancer (HDGC), Hurthle cell cancer (oxyphil cell carcinoma), Insulinoma, Islet cell tumor, Keratoacanthoma, Klatskin tumor, Large cell neuroendocrine carcinoma, Leiomyosarcoma, Leydig cell tumor, Lip cancer, Liposarcoma, Lymphomatoid papulosis, Lymphoplasmacytic lymphoma, Malignant mesenchymoma, Malignant mixed mullerian tumor, Malignant peripheral nerve sheath tumor (MPNST), Malignant rhabdoid tumor of the kidney, Medulloepithelioma, Meningioma, Mesoblastic nephroma, Metaplastic cancer of the breast, Monoclonal gammopathy of undetermined significance (MGUS), Mouth cancer, Mucinous cystic neoplasm, Mucoepidermoid carcinoma, Muscle cancer (myosarcoma), Myoepithelial carcinoma, Mycosis fungoides, Myelofibrosis, Myxofibrosarcoma, Nephroblastoma, Neuroendocrine carcinoma of the skin, NUT carcinoma, Oat cell cancer, Occult primary cancer, Ocular or intraocular melanoma, Olfactory neuroblastoma (esthesioneuroblastoma), Oligodendroglioma, Oncocytic carcinoma, Ovarian small cell cancer, Paget disease, Pagetoid reticulosis, Paraganglioma, Parathyroid cancer, Periosteal osteosarcoma, Peripheral primitive neuroectodermal tumor (PPNET), Pheochromocytoma, Phyllodes tumor, Pineoblastoma, Plasmacytoma, Polycythemia vera, Polymorphous low-grade adenocarcinoma, Primary cutaneous lymphoma, Primary peritoneal carcinoma, Prolactinoma (lactotroph adenoma), Renal cell carcinoma, Sarcomatoid carcinoma (carcinosarcoma), Schwannoma, Sclerosing epithelioid fibrosarcoma, Sebaceous carcinoma, Seminoma, Sertoli cell tumor, Sezary syndrome, Sinus cancer, Skin adnexal tumors, Solid pseudopapillary neoplasm, Solitary fibrous tumor, Solitary plasmacytoma, Octreotideoma, Spermatocytic seminoma, Spindle cell neoplasm, spindle cell tumor, spindle cell carcinoma, spindle cell sarcoma, Subcutaneous panniculitis-like T-cell lymphoma, Synovial sarcoma, T-cell lymphoma, Teratoma, Throat cancer, Thymoma, Tongue cancer, Tonsil cancer, Trabecular cancer, Translocation renal cell carcinoma, Transitional cell carcinoma (urothelial carcinoma), Undifferentiated pleomorphic sarcoma, Urachal cancer, Urethral cancer, Urothelial carcinoma (transitional cell carcinoma), Uterine cancer, Verrucous carcinoma, VIPoma, Vocal cord/voice box cancer, Womb cancer, or Yolk sac tumor.

Non-Cancerous Conditions

In another aspect, the invention provides a method of treating a non-cancerous condition in a subject in need thereof, the method comprising: administering to the subject an effective amount of a therapeutic agent comprising a combination of the conjugates described above and a pharmaceutically acceptable carrier or excipient.

In certain embodiments, the non-cancerous condition is a musculoskeletal disorders or a tissue hypertrophy disorder. In still other embodiments, the subject is a human.

Efficacy Measurements of Biological Systems.

In another aspect, the disclosure encompasses a method of measuring the efficacy of a biological system of a subject. In particular embodiments, the biological system to be measured or monitored is the renal system, the hepatic system, or the blood pool.

In particular embodiments, the method of measuring the efficacy of a biological system includes:

(a) administering a quantifiable amount of a diagnostic agent comprising a combination of imaging agent conjugates and a pharmaceutically acceptable carrier or excipient to the subject;
(b) imaging the subject with positron emission tomography (PET), single-photon emission computerized tomography (SPECT), or magnetic resonance imaging (MRI); and
(c) determining the amount of therapeutic agent present in the biological system being observed in the subject.

In a particular aspect, the disclosure encompasses a method of measuring the efficacy of renal function a subject. In particular embodiments, the method comprises:

(a) administering a quantifiable amount of a diagnostic agent comprising a combination of imaging agent conjugates and a pharmaceutically acceptable carrier or excipient to the subject;
(b) imaging the subject with positron emission tomography (PET), single-photon emission computerized tomography (SPECT), or magnetic resonance imaging (MRI); and
(c) determining the amount of therapeutic agent present in the biological system being observed in the subject.

In another aspect, the invention provides a method of quantifying the glomerula filtration rate of a subject. In particular embodiments, the method comprises:

(a) administering a quantifiable amount of a diagnostic agent comprising a combination of imaging agent conjugates and a pharmaceutically acceptable carrier or excipient to the subject; and
(b) determining the amount of diagnostic agent present in the blood and urine of the subject as a function of time using either measurements of each bodily fluid or imaging the subject with positron emission tomography (PET), single-photon emission computerized tomography (SPECT), or magnetic resonance imaging (MRI).

Radiosurgery

Radiosurgery is a known method of treating targets in the body. During radiosurgery, the target is bombarded with a series of X-ray beams fired from various different positions and orientations by using a radiation delivery system, to affect the tumor biology using the cumulative radiation dose at the target. The radiation can be delivered invasively in conjunction with traditional scalpel surgery, or through a percutaneous catheter. CyberKnife™ (Accuray Inc.) and Trilogy™ (Varian Medical Systems) are two such radiation delivery systems. Advances in stereotactic surgery have provided increased accuracy in registering the position of tissue targeted for treatment and a radiation source. For example, see U.S. Pat. Nos. 6,351,662 and 6,402,762. Stereotactic radiosurgery systems may be commercially available from ACCURAY, INC. of Sunnyvale, Calif, and BRAINLAB. The Accuray Cyberknife™ stereotactic radiosurgery system has reportedly been used to provide targeted, painless, and fast treatment of tumors.

In one aspect, the invention provides a radiosurgical method for treating a patient body, the method comprising:

receiving a desired lesion pattern and planned radiation distribution;
administering an effective amount of a diagnostic agent comprising a combination of imaging agent conjugates and a pharmaceutically acceptable carrier or excipient to the subject to effectively image the desired lesion pattern; and
performing surgery on the desired lesion pattern to treat the patient body.

In certain embodiments, the surgery can be using scalpel surgery or a stereotactic radiosurgery system to administer a cumulative radiation dose.

In other embodiments, the imaging agent conjugates of the diagnostic agent further comprises one or more targeting ligands wherein the one or more targeting ligands are cRGD, PSMA, FAP, bombesin, octreotide, octreotide, or a dimer formed from their combination.

In still other embodiments, the desired lesion pattern is received from a user interface of a treatment planning module. Such planning modules can be pre-programmed with specifications for various disease states and cancerous conditions. Alternatively, specifications for desired lesion patterns can be identified and produced using artificial intelligence data.

EXAMPLES

Example 1: Combinations of Imaging Agent Conjugates

A combination of imaging agent conjugates includes any two or more of the imaging agent conjugates cRGD-ZW800-1, KUE-ZW800-1, FAP-ZW800-1, bombesin-ZW800-1, octreotide-ZW800-1; cRGD-ZW700-1 Forte, KUE-ZW700-01 Forte, FAP-ZW700-1 Forte, bombesin-ZW700-1 Forte, octreotide-ZW700-1 Forte; cRGD-ZW830-1, KUE-ZW830-01, FAP-ZW830-1, bombesin-ZW830-1, octreotide-ZW830-1; cRGD-ZW-DOTA, KUE-ZW-DOTA, FAP-ZW-DOTA, bombesin-ZW-DOTA, octreotide-ZW-DOTA; cRGD-ZW-PyC3A, KUE-ZW-PyC3A, FAP-ZW-PyC3A, bombesin-ZW-PyC3A, octreotide-ZW-PyC3A; cRGD-ZW-Macropa, KUE-ZW-Macropa, FAP-ZW-Macropa, bombesin-ZW-Macropa, octreotide-ZW-Macropa; cRGD-ZW-porphyrin, KUE-ZW-porphyrin, and, FAP-ZW-porphyrin, bombesin-ZW-porphyrin, octreotide-ZW-porphyrin.

Combination 1: A particular combination of imaging agent conjugates includes imaging agent conjugates cRGD-ZW800-1, KUE-ZW800-1, and FAP-ZW800-1.

Combination 2: A particular combination of imaging agent conjugates includes imaging agent conjugates cRGD-ZW700-1 Forte, KUE-ZW700-1 Forte, and FAP-ZW700-1 Forte.

Combination 3: A particular combination of imaging agent conjugates includes imaging agent conjugates cRGD-ZW830-1, KUE-ZW830-1, and FAP-ZW830-1.

Combination 4: A particular combination of imaging agent conjugates includes imaging agent conjugates cRGD-ZW800-1, and KUE-ZW700-1 Forte.

Combination 5: A particular combination of imaging agent conjugates includes imaging agent conjugates KUE-ZW800-1, and cRGD-ZW700-1 Forte.

Combination 6: A particular combination of imaging agent conjugates includes imaging agent conjugates KUE-ZW800-1, and FAP-ZW700-1 Forte.

Combination 7: A particular combination of imaging agent conjugates includes imaging agent conjugates FAP-ZW800-1, and KUE-ZW700-1 Forte.

Combination 8: A particular combination of imaging agent conjugates includes imaging agent conjugates FAP-ZW800-1, and cRGD-ZW700-1 Forte.

Combination 9: A particular combination of imaging agent conjugates includes imaging agent conjugates cRGD-ZW800-1, and FAP-ZW700-1 Forte.

Combination 10: A particular combination of imaging agent conjugates includes imaging agent conjugates cRGD-ZW-DOTA-Cu-64, KUE-ZW-DOTA-Cu-64, and FAP-ZW-DOTA-Cu-64.

Combination 11: A particular combination of imaging agent conjugates includes imaging agent conjugates CRGD-ZW-DOTA-Lu-177, KUE-ZW-DOTA-Lu-177, and FAP-ZW-DOTA-Lu-177.

Example 2: Imaging of Organisms

The FLARE™ Image-Guided Surgery System is a continuous-wave (CW) intraoperative imaging system that is capable of simultaneous, real-time acquisition and display of color video (i.e., surgical anatomy) and two channels of invisible NIR fluorescent (700 nm and 800 nm) light. Details of the theory, engineering, and operation of the imaging system has been described in detail previously. See, Tanaka, E., H. S. Choi, H. Fujii, M. G. Bawendi, and J. V. Frangioni, Image-guided oncologic surgery using invisible light completed: pre-clinical development for sentinel lymph node mapping. Ann Surg Oncol, 2006. 13: 1671-81; De Grand, A. M. and J. V. Frangioni, An operational near-infrared fluorescence imaging system prototype for large animal surgery. Technol Cancer Res Treat, 2003. 2: 553-562; and Nakayama, A., F. del Monte, R. J. Hajjar, and J. V. Frangioni, Functional near-infrared fluorescence imaging for cardiac surgery and targeted gene therapy. Molecular Imaging, 2002. 1: 365-377, each of which is incorporated herein by reference.

Specifications for the FLARE™ Image-Guided Surgery System is provided in Table 1 below.

TABLE 1

FLARE ™ NIR Fluorescence Imaging System Specifications

| Category | Specification | Description |
|---|---|---|
| Physical | Size | Mobile Cart: 32" W × 32" D × 41.4" H; Mast Height: 82" |
| | Weight | 675 lbs, including all electronics |
| | Arm | 6-degree-of-freedom; Reach: 43"-70" from floor, 50.7" from cart |
| Electrical | Voltage and Plug | 120 V AC, 60 Hz; single NEMA 5-15 120 V/15 A AC plug |
| | Current | 15 A max |
| | Grounding | Isolation transformer for all components; redundant chassis grounding |
| | Leakage Current | <300 μA (per AAMI/IEC #60601) |
| Sterility | Shield | Disposable acrylic shield with ≥95% transmission |
| | Drape | Disposable, custom-fit plastic drape bonded to shield |
| Light Source | Housing | Anodized aluminum with secondary 400 W cooling |
| | Elements | Custom 25 mm circular LED arrays w/integrated linear |
| | Electronics | Custom passive and active boards with embedded controller |
| | Fluence Rates | 40,000 1x white light (400-650 nm), 4 mW/cm$^2$ of 700 nm (656-678 nm) excitation light, 14 mW/cm$^2$ of 800 |

TABLE 1-continued

FLARE ™ NIR Fluorescence Imaging System Specifications

| Category | Specification | Description |
|---|---|---|
| Optics | Working Distance | 18" from surface of patient |
| | Field-of-View | 2.2 W × 1.7 H cm to 15 W × 11.3 cm (adjustable zoom) |
| | Emission/ Reflectance Channels | Color Video (400-650 nm), 700 nm fluorescence (689-725 nm), 800 nm fluorescence (800-848 nm), all with |
| | Pixel Resolution | 640 × 480 for each camera |
| | System Resolution | 125 × 125 μm (x, y) to 625 × 625 μm (x, y) |
| | Display Refresh | Up to 15 Hz simultaneous acquisition on all 3 camera |
| | NIR Exposure Time | Adjustable from 100 μsec to 8 sec |
| Hands-Free | Optics | Automatic zoom/focus |
| | Control | 6-pedal footswitch |
| Monitors | Number | 2 cart-mounted 20" for operator; 1 satellite 20" on stand for surgeon |

Example 3: In Vivo Characterization of Combination of Conjugates

For in vivo characterization, 40 pmol/g (average 10 nmol) of Combination 1 can be injected IV into 25 g athymic nude mice harboring xenograft human tumors. The FLARE™ imaging system can be set to a 665 nm excitation fluence rate of 1 mW/cm$^2$. Simultaneous color video and NIR fluorescence (800 nm) images can be acquired pre-injection, every 1 sec for the first 20 sec then every 1 min for 2 h. Camera acquisition can be held constant (typically 100 msec) and chosen to ensure that all intensity measurements are within the linear range of the 12-bit Orca-AG (Hamamatsu) NIR camera. Blood can be sampled at 0, 1, 2, 5, 10, 15, 30, 60, and 120 min via tail vein. Intensity-time curves for all major organs and tissues can be quantified. The peak fluorescence intensity and time can be determined for each tumor/tissue/organ, along with the intensity in each at 1 h post-injection.

Example 4: In Vitro Optical and Stability Properties of Combination of Conjugates cRGD-ZW700-1c ZW700-1c, and ZW-800-1 are shown in FIG. 1 and are characterized with respect to their optical properties and stability in vitro. Commercial NIR fluorophores, such as IRDye™800-RS (RS-800), IRDye800-CW (CW-800), Cy5.5, and Cy7 have various degrees of sulfonation in order to achieve aqueous solubility.

The normalized absorbance of ZW800-1 and ZW700-1c in 37° C. buffered FBS, pH 7.4 over time from 0 to 60 hours are shown in FIGS. 2-4. Note is made of the extreme stability of ZW700-1c compared to ZW800-1. Corresponding changes in absorption spectra during metabolism in warm serum is shown in FIGS. 5-6. Note is made of high stability of ZW700-1c over time, particularly as compared to ZW800-1.

cRGD is stable in serum for days. Data generated in the same way is expected to show that cRGD-ZW700-1c has further increased stability as compared to compared to ZW700-1c, ZW700-1c, ZW800-1 and cRGD-ZW800-1. In particular, cRGD-ZW700-forte is expected to have significant improvements in providing prolonged targeted imaging of tumors overexpressing integrins as compared to ZW700-

1c, ZW800-1 and cRGD-ZW800-1. In addition, cRGD-ZW700-forte is expected to produce a brighter signal at a lower dose than as compared to ZW700-1c, ZW800-1 and cRGD-ZW800-1.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Those skilled in the art will recognize, or be able to ascertain using no more than routine experimentation, many equivalents to the specific embodiments of the invention described herein.

Such equivalents are intended to be encompassed by the following claims.

The invention claimed is:

1. A composition comprising a combination of imaging agents which absorb invisible near-infrared fluorescent light at the same wavelength; wherein the composition comprises a combination of:

a) cRGD-ZW800-1, KUE-ZW800-1, and FAP-ZW800-1;
b) cRGD-ZW700-1 Forte, KUE-ZW700-1 Forte, and FAP-ZW700-1 Forte; or
c) cRGD-ZW830-1, KUE-ZW830-1, and FAP-ZW830-1.

2. A method of imaging cells, the method comprising:

a) contacting cells with a composition according to claim 1,
b) irradiating the cells at a wavelength absorbed by the combination of imaging agents; and
c) and detecting a signal from the combination of imaging agents, thereby imaging the cells.

3. The method of claim 2, wherein the cells are tumor cells, inflammatory cells, or cells undergoing angiogenesis.

4. The method of claim 2, wherein the combination of imaging agents is administered to an organism comprising or suspected of comprising the cells.

5. The method of claim 4, wherein the organism is human.

6. The method of claim 2, wherein the cells are is imaged in vivo.

* * * * *